(12) United States Patent
Byerly et al.

(10) Patent No.: US 11,771,837 B2
(45) Date of Patent: Oct. 3, 2023

(54) MEDICATION DELIVERY DEVICE WITH SENSING SYSTEM

(71) Applicant: Eli Lilly and Company, Indianapolis, IN (US)

(72) Inventors: Roy Howard Byerly, Indianapolis, IN (US); Daniel Joseph Nelsen, Central Falls, RI (US); Russell Wayne Perkins, Carmel, IN (US); Robert Charles Uschold, Leominster, MA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/880,879

(22) Filed: Aug. 4, 2022

(65) Prior Publication Data

US 2022/0370725 A1 Nov. 24, 2022

Related U.S. Application Data

(63) Continuation of application No. 16/632,730, filed as application No. PCT/US2018/046585 on Aug. 14, 2018, now Pat. No. 11,471,608.

(Continued)

(51) Int. Cl.
*A61M 5/315* (2006.01)

(52) U.S. Cl.
CPC .... *A61M 5/31568* (2013.01); *A61M 5/31551* (2013.01); *A61M 2205/0294* (2013.01); *A61M 2205/3327* (2013.01)

(58) Field of Classification Search
CPC .......... A61M 5/31568; A61M 5/31551; A61M 5/20; A61M 5/3155; A61M 2205/52;

(Continued)

(56) References Cited

U.S. PATENT DOCUMENTS

| 5,509,905 A | 4/1996 | Michel |
| 5,536,240 A | 7/1996 | Edwards et al. |

(Continued)

FOREIGN PATENT DOCUMENTS

| CA | 3073279 | 2/2019 |
| CN | 108030978 A | 5/2018 |

(Continued)

OTHER PUBLICATIONS

Patent Cooperation Treaty International Search Report pertaining to International Application No. PCT/US2018/046585; International Filing Date: Aug. 14, 2018; dated Oct. 31, 2018.

(Continued)

*Primary Examiner* — Nathan R Price
*Assistant Examiner* — Anh Bui
(74) *Attorney, Agent, or Firm* — Arthur C. H. Shum

(57) ABSTRACT

Medication delivery devices are provided having a dose delivery sensing capability. A sensed element is attached to a dose setting member of the device. The sensed element includes surface features radially-spaced from one another. A rotational sensor is attached to an actuator of the device. The rotational sensor includes a movable element that is contactable against the surface features. The rotational sensor is configured to generate a signal in response to the movement of the movable element over the surface features during their rotation. A controller is operatively coupled to the rotational sensor, and in response to receiving the generated signal, the controller is configured to determine a number of the surface features passing the movable element of the rotational sensor during dose delivery. The number can be associated with an amount of dose delivered. Sensing can be provided in a module or integrated in device.

5 Claims, 11 Drawing Sheets

Related U.S. Application Data

(60) Provisional application No. 62/676,576, filed on May 25, 2018, provisional application No. 62/547,928, filed on Aug. 21, 2017.

(58) Field of Classification Search
CPC .. A61M 2205/0294; A61M 2205/3327; A61M 2205/3375; A61M 2205/502
See application file for complete search history.

(56) References Cited

U.S. PATENT DOCUMENTS

| | | | |
|---|---|---|---|
| 5,536,249 A | 7/1996 | Castellano et al. | |
| 5,728,074 A | 3/1998 | Castellano et al. | |
| 5,951,398 A | 9/1999 | Yamamoto et al. | |
| 6,138,669 A | 10/2000 | Rocci, Jr. et al. | |
| 6,277,099 B1 | 8/2001 | Strowe et al. | |
| 6,585,698 B1 | 7/2003 | Packman et al. | |
| 7,008,399 B2 | 3/2006 | Larsen et al. | |
| 7,195,616 B2 | 3/2007 | Diller et al. | |
| 7,749,786 B2 | 7/2010 | Wells | |
| 8,221,356 B2 | 7/2012 | Enggaard et al. | |
| 8,257,319 B2 | 9/2012 | Plumptre | |
| 8,556,865 B2 | 10/2013 | Krulevitch et al. | |
| 8,579,867 B2 | 11/2013 | Harms et al. | |
| 9,078,973 B2 | 7/2015 | Harms et al. | |
| 9,186,465 B2 | 11/2015 | Jorgensen et al. | |
| 9,345,838 B2 | 5/2016 | Plumptre | |
| 9,616,178 B2 | 4/2017 | Butler et al. | |
| 9,636,464 B1 | 5/2017 | Binier | |
| 9,649,448 B2 | 5/2017 | Madsen | |
| 9,675,761 B2 | 6/2017 | Hoeholt et al. | |
| 9,750,886 B2 | 9/2017 | Plambech et al. | |
| 9,764,095 B2 | 9/2017 | Draper | |
| 9,833,576 B2 | 12/2017 | Windum et al. | |
| 10,004,852 B2 | 6/2018 | Marsh et al. | |
| 10,383,996 B2 | 8/2019 | Miller et al. | |
| 10,420,895 B2 | 9/2019 | Erbstein et al. | |
| 10,682,469 B2 | 6/2020 | Jakobsen et al. | |
| 11,471,608 B2* | 10/2022 | Byerly | A61M 5/31551 |
| 2001/0034506 A1 | 10/2001 | Hirschman et al. | |
| 2002/0120655 A1 | 8/2002 | Liu et al. | |
| 2004/0210199 A1 | 10/2004 | Atterbury et al. | |
| 2006/0153693 A1 | 7/2006 | Fiechter et al. | |
| 2009/0069742 A1 | 3/2009 | Larsen | |
| 2011/0270214 A1 | 11/2011 | Joergensen et al. | |
| 2014/0074041 A1 | 3/2014 | Pedersen et al. | |
| 2014/0194829 A1 | 7/2014 | Baek et al. | |
| 2014/0276583 A1 | 9/2014 | Chen et al. | |
| 2014/0312074 A1 | 10/2014 | Madsen et al. | |
| 2015/0032059 A1 | 1/2015 | Allerdings et al. | |
| 2015/0290396 A1 | 10/2015 | Nagar et al. | |
| 2015/0367077 A1 | 12/2015 | Plambech et al. | |
| 2016/0008552 A1 | 1/2016 | Madsen et al. | |
| 2016/0030680 A1 | 2/2016 | Veasey et al. | |
| 2016/0030683 A1 | 2/2016 | Taylor et al. | |
| 2016/0082192 A1 | 3/2016 | Veasey et al. | |
| 2016/0213853 A1 | 7/2016 | Despa et al. | |
| 2016/0239610 A1 | 8/2016 | Andersen et al. | |
| 2016/0287804 A1 | 10/2016 | Madsen et al. | |
| 2016/0287807 A1 | 10/2016 | Madsen et al. | |
| 2016/0378951 A1 | 12/2016 | Gofman et al. | |
| 2017/0368263 A1 | 12/2017 | Ploch | |
| 2018/0126088 A1 | 5/2018 | Radmer et al. | |
| 2018/0147363 A1 | 5/2018 | Hansen et al. | |
| 2018/0353700 A1 | 12/2018 | Säll et al. | |
| 2018/0369488 A1 | 12/2018 | Carlsson et al. | |
| 2018/0369494 A1 | 12/2018 | Grubbe | |
| 2019/0022328 A1 | 1/2019 | Schleicher et al. | |
| 2019/0022330 A1* | 1/2019 | Schleicher | A61M 5/31551 |
| 2019/0054251 A1 | 2/2019 | Pieronek et al. | |
| 2019/0083708 A1 | 3/2019 | Säll | |

FOREIGN PATENT DOCUMENTS

| | | |
|---|---|---|
| CN | 108392698 A | 8/2018 |
| CN | 105263546 | 7/2019 |
| EP | 2060284 | 5/2009 |
| EP | 3162398 | 5/2017 |
| JP | 2004526486 | 9/2004 |
| JP | 2015527128 | 9/2015 |
| JP | 2017500090 A | 1/2017 |
| WO | 1990009202 | 8/1990 |
| WO | 1996019872 | 6/1996 |
| WO | 200264196 | 8/2002 |
| WO | 2003005891 | 1/2003 |
| WO | 2006045525 | 5/2006 |
| WO | 2009062675 | 5/2009 |
| WO | 2014020008 | 2/2014 |
| WO | 2014180744 | 11/2014 |
| WO | 2015075136 | 5/2015 |
| WO | 2016007935 | 1/2016 |
| WO | 2016180873 | 11/2016 |
| WO | 2016193229 | 12/2016 |
| WO | 2017092960 | 6/2017 |
| WO | 2017097507 | 6/2017 |
| WO | 2017114768 | 7/2017 |
| WO | 2017118705 | 7/2017 |
| WO | 2017120178 | 7/2017 |
| WO | 2017148855 | 9/2017 |
| WO | 2017200989 | 11/2017 |
| WO | 2018013419 | 1/2018 |
| WO | 2018099795 | 6/2018 |
| WO | 2018104289 | 6/2018 |
| WO | 2018125887 | 7/2018 |
| WO | 2018138016 | 8/2018 |
| WO | 2018141571 | 8/2018 |
| WO | 2019018793 | 1/2019 |
| WO | 201936576 | 2/2019 |
| WO | 2019121610 | 6/2019 |

OTHER PUBLICATIONS

Patent Cooperation Treaty Written Opinion of the International Searching Authority pertaining to International Application No. PCT/US2018/046585; International Filing Date: Aug. 14, 2018; dated Oct. 31, 2018.

\* cited by examiner

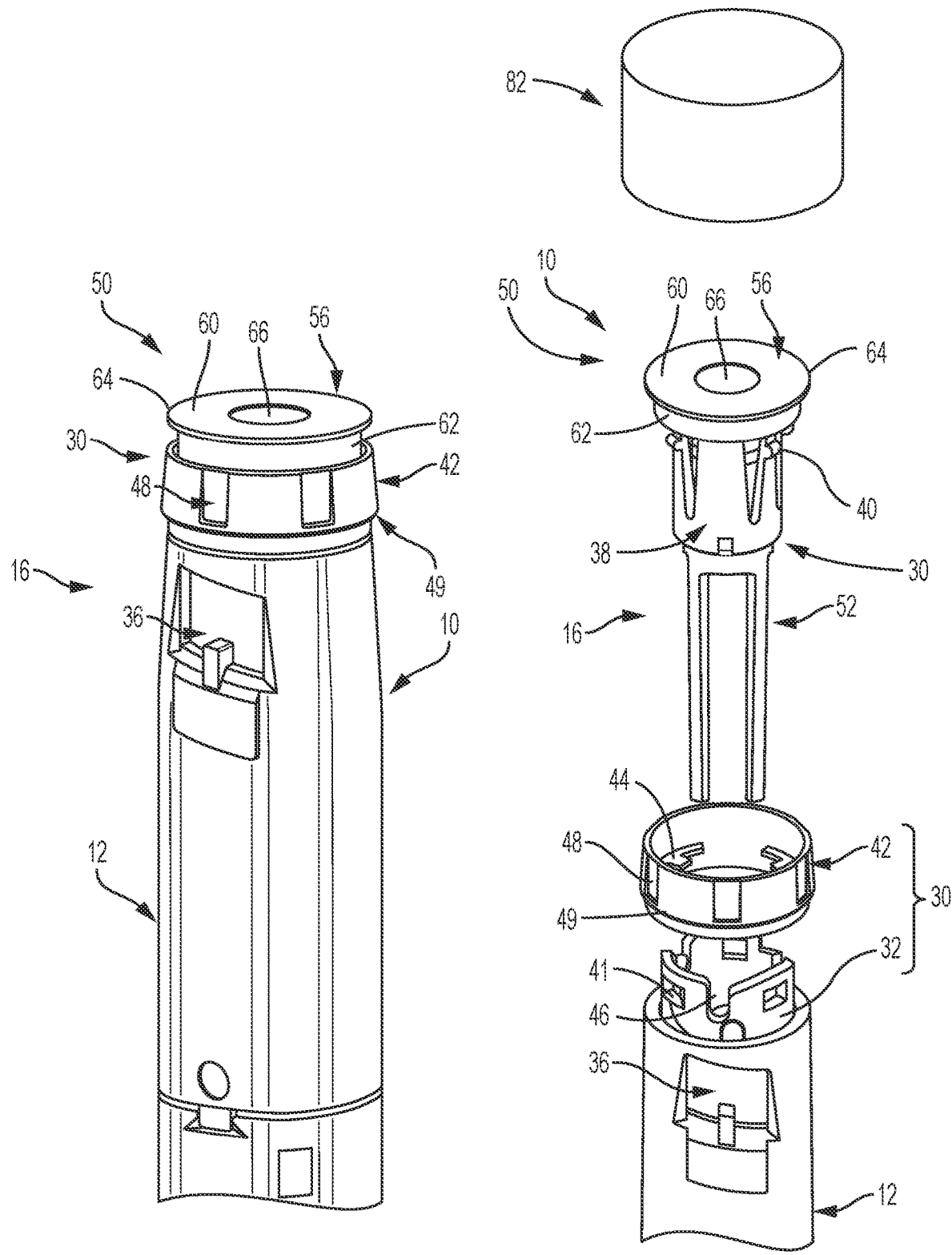

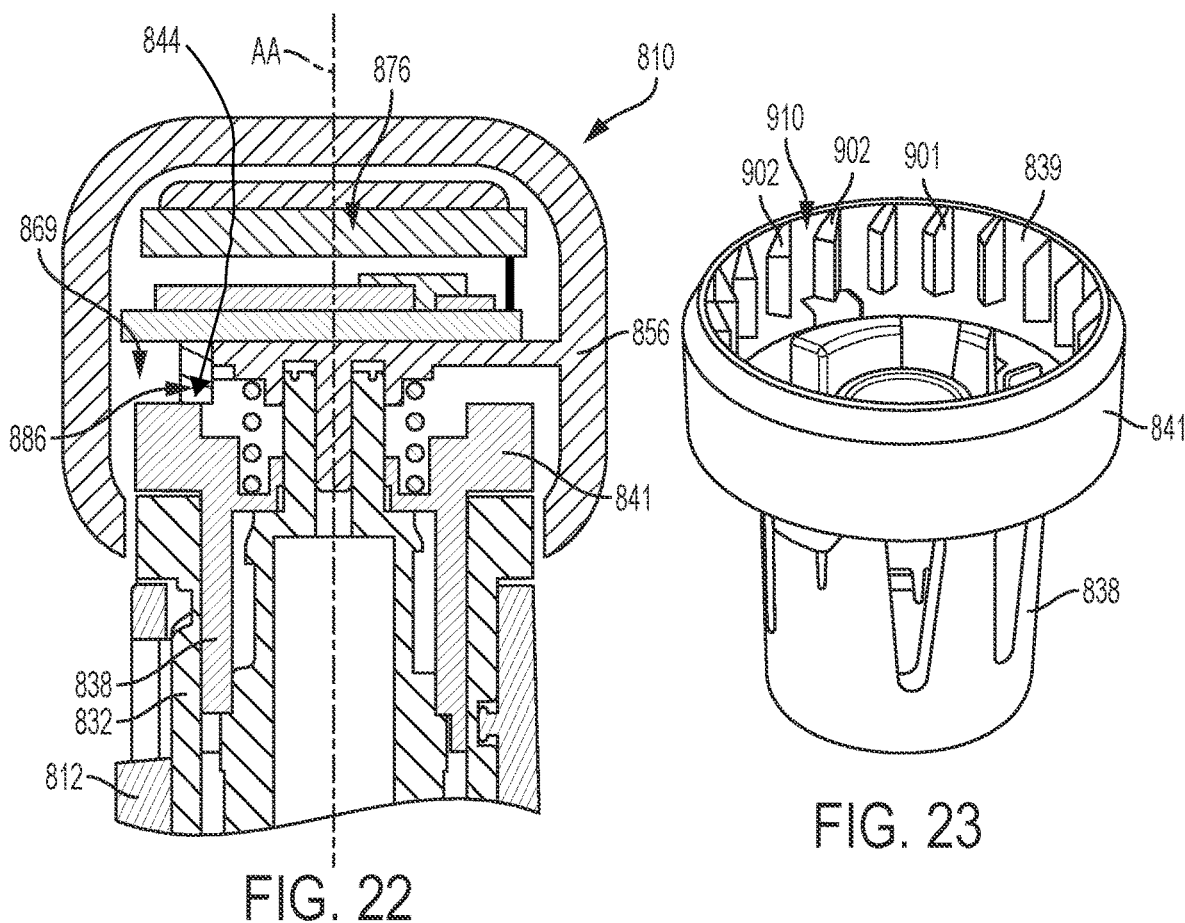
FIG. 22
FIG. 23
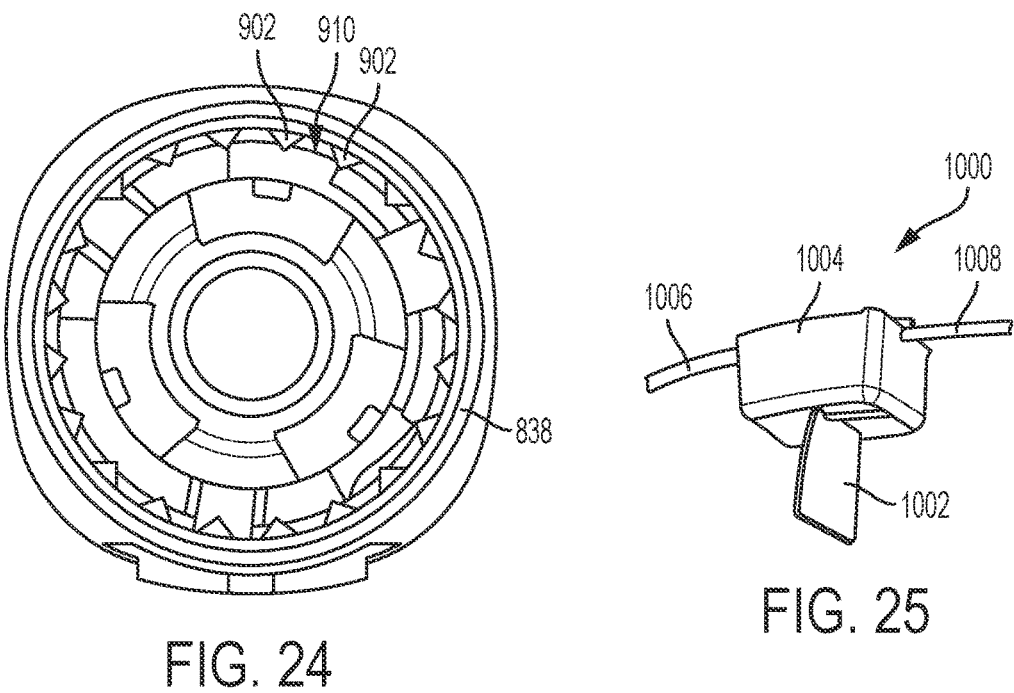
FIG. 24
FIG. 25

MEDICATION DELIVERY DEVICE WITH SENSING SYSTEM

BACKGROUND

The present disclosure relates to an electronic dose detection system for a medication delivery device and/or a module adapted to removably attach to a proximal end portion of a medication delivery device. The dose delivery detection system is operable to detect data for determining the amount of a dose of medication delivered by the medication delivery device.

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Systems to measure the relative movement of members of a medication delivery device have been developed in order to assess the dose delivered. Yet, systems integrated into the device or module for high volume manufacturing and repeatable accuracy during the product's lifecycle have been challenging to design. The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event, and/or overcome one or more of these and other shortcomings of the prior art.

SUMMARY OF THE DISCLOSURE

In one embodiment, a medication delivery device is provided, including a device body, a dose setting member attached to the device body and rotatable relative to the device body about an axis of rotation during dose delivery. The dose setting member includes a sensed element including surface features radially-spaced from one another about the axis of rotation of the dose setting member. An actuator or a dose button is attached to the device body. The sensed element is rotatable relative to the dose button during dose delivery in relation to the amount of dose delivered. A rotational sensor includes a movable element contactable against the surface features of the sensed element. The dose button may be configured to house the rotational sensor. The movable element is positioned to move over the surface features during rotation of the sensed element relative to the dose button during dose delivery. The rotational sensor is configured to generate a signal in response to the movement of the movable element over the surface features during the rotation of the dose setting member. A controller is operatively coupled to the rotational sensor and may be housed by the dose button or a module. In response to receiving the generated signal from the rotational sensor, the controller is configured to determine a number of the surface features passing the movable element of the rotational sensor during dose delivery.

In another embodiment of a medication delivery device, an actuator has a first position in which a movable element of a rotational sensor is disengaged from axially extending surface features, and a second position in which the movable element of the rotational sensor is contactable with the axially extending surface features. The actuator may be a dose button. When the actuator is in the second position, a controller is configured, upon receiving a signal indicative of contact with an initial first one of the axially extending surface features, to activate the controller to a full power state, and the controller is configured, upon receiving a signal indicative of contact with a subsequent one of the axially extending surface features after the initial first one, to determine a number of the axially extending surface features passing the movable element of the rotational sensor during dose delivery.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

FIG. 3 is a perspective view of the proximal portion of the exemplary medication delivery device of FIG. 1.

FIG. 4 is a partially-exploded, perspective view of the proximal portion of the exemplary medication delivery device of FIG. 1, and showing a dose detection module.

FIG. 22 is a side, diagrammatic view, partially in cross section, of a proximal portion of another embodiment of a medication delivery device with a dose detection system, with its dose button in a proximal position.

FIG. 23 is a perspective view of another example of a flange with another example of surface features along an inner radial surface.

FIG. 24 is an axial top view of the proximal portion of the medication delivery device of FIG. 22, depicting the arrangement of the surface features.

FIG. 25 is a perspective view of another example of a rotational sensor, shown as a piezoelectric sensor.

DETAILED DESCRIPTION

Figure 1:
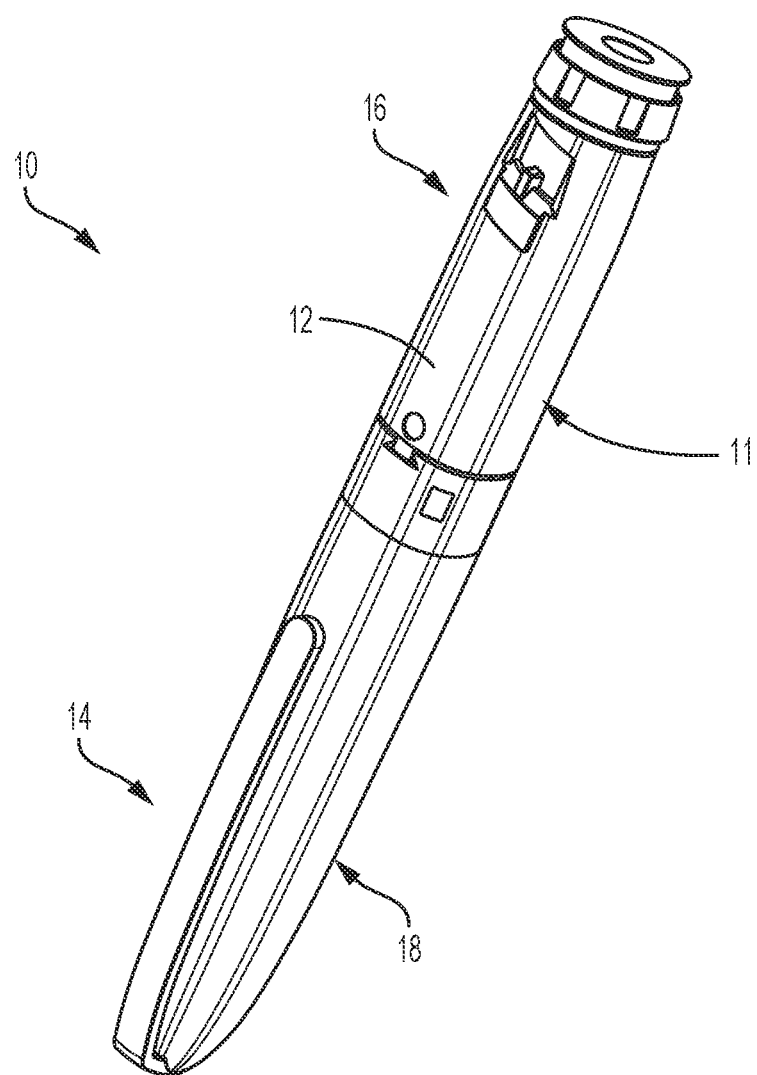
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for sensing of relative rotational movement between a dose setting member and an actuator of the medication delivery device in order to determine the amount of a dose delivered by a medication delivery device. The sensed relative rotational movements are correlated to the amount of the dose delivered. By way of illustration, the medication delivery device is described in the form of a pen injector. However, the medication delivery device may be any device which is used to set and to deliver a dose of a medication, such as pen injectors, infusion pumps and syringes. The medication may be any of a type that may be delivered by such a medication delivery device.

Devices described herein, such as a device 10, 210, 410, 610 or 810, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
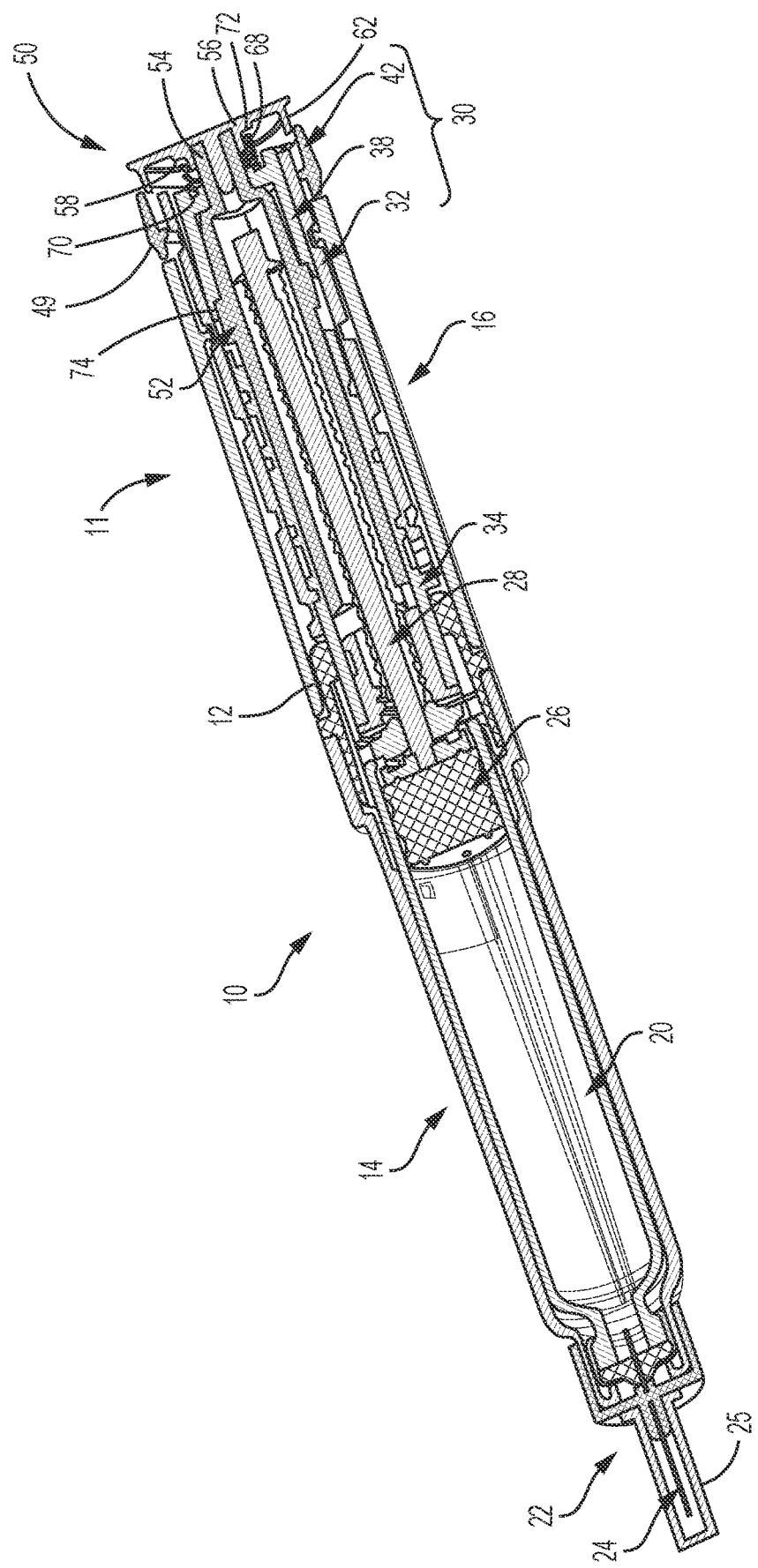
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Device 10 includes a body 11 comprising an elongated, pen-shaped housing 12 including a distal portion 14 and a proximal portion 16. Distal portion 14 is received within a pen cap 18. Referring to FIG. 2, distal portion 14 contains a reservoir or cartridge 20 configured to hold the medicinal fluid to be dispensed through its distal outlet end during a dispensing operation. The outlet end of distal portion 14 is equipped with a removable needle assembly 22 including an injection needle 24 enclosed by a removable cover 25. A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultaneously move axially and rotationally) about a longitudinal axis AA of rotation relative to housing 12 during dose setting and dose dispensing. FIGS. 1-2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection. The extended positon may be any position between a position corresponding to an incremental extended position (such as a dose setting a 0.5 or 1 unit) to a fully extended position corresponding to a maximum dose deliverable by device 10 in a single injection and to screw into housing 12 in a distal direction until it reaches the home or zero position corresponding to a minimum dose deliverable by device 10 in a single injection.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dose dial member 32 by detents 40 received within openings 41 in dial member 32. In one example, dose setting member 30 further includes an optional collar or skirt 42 positioned around the outer periphery of dial member 32 at its proximal end. Skirt 42 is axially and rotationally locked to dial member 32 by tabs 44 received in slots 46.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dial member 32 and, as described later, cooperates with a clutch to selectively couple dial member 32 with a dose button. As shown, skirt 42 provides a surface external of body 11 to enable a user to rotate dose dial member 32 for setting a dose.

Figure 18:
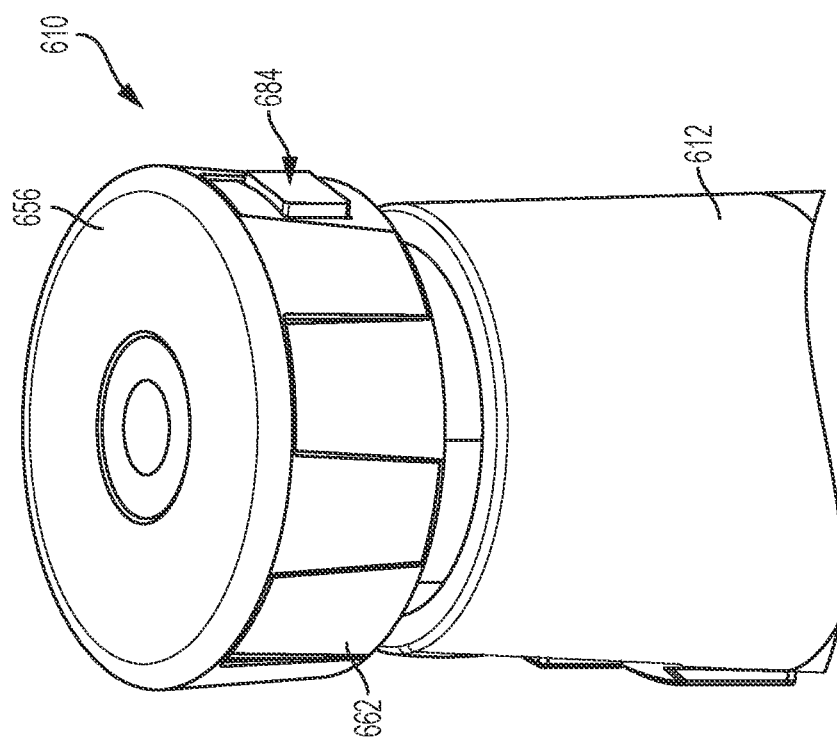
FIG. 18 is a perspective view of a proximal portion of another embodiment of a medication delivery device with a dose detection system.

In the embodiment illustrated in FIG. 18, the dose button of the illustrated device 10 is one-piece component which combines both skirt 42 and the dose button 56 of FIG. 1-4. In this embodiment, the flange is attached to the dial member and cooperates with a clutch, described below, to selectively couple the dial member with the one-piece dose button, shown as button 656. The radial exterior surface of one-piece dose button 656 provides a surface external of the device body 11 to rotate the dial member.

Skirt 42 illustratively includes a plurality of surface contours 48 and an annular ridge 49 formed on the outer surface of skirt 42. Surface contours 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose dial member 32 for dose setting.

Delivery device 10 includes an actuator 50 having a clutch 52 which is received within dose dial member 32. Clutch 52 includes an axially extending stem 54 at its proximal end. Actuator 50 further includes dose button 56 positioned proximally of skirt 42 of dose setting member 30, as shown. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between. Face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation. In an alternative embodiment, skirt 42 is omitted from the device, and the annular wall portion 62 of dose button 56 extends distally to a location approximately to the distal extent of the skirt relative to the dial member as shown in the figures.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 (when employed) are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow backdriving rotation of dose setting member 30 relative to actuator 50 and housing 12. Also, since dose setting member 30 and actuator 50 are free to relatively rotate, actuator 50 is held from rotating relative to device housing 12 by the user's engagement of dose button 56 by pressing against it.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The dose delivered may be derived based on the rotation of dose setting member 30 relative to actuator 50 during dose delivery. This rotation may be determined by detecting the incremental movements of the dose setting member which are "counted" as the dose setting member is rotated during dose delivery.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference in its entirety, where such device being modified with one or more various sensor systems described herein to determine an amount of medication delivered from the medication delivery device based on the sensing of relative rotation within the medication delivery device. Another example of the delivery device is a reusable pen device that may be found in U.S. Pat. No. 7,195,616, entitled "Medication Injector Apparatus with Drive Assembly that Facilitates Reset," which is hereby incorporated by reference in its entirety, where such device being modified with one or more various sensor systems described herein to determine an amount of medication delivered from the medication delivery device based on the sensing of relative rotation within the medication delivery device.

The dose detection systems use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from attachment where the components/members are coupled by one or more intermediate functional members, such as the way dose dial member 32 is coupled in FIG. 2 to dose button 56 by clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position or movement of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose detection system, the sensed component rotates relative to the sensing component, which is able to detect the rotational movement of the sensed component. The sensing component may comprise one or more sensing elements, and the sensed component may comprise one or more sensed elements. The sensor system detects the movement of the sensed component and provides outputs representative of the movement of the sensed component.

Illustratively, the dose detection system includes an electronics assembly suitable for operation of the sensor system as described herein. A controller is operably connected to the sensor system to receive outputs from the rotational sensor. The controller begins receiving generated signals from the rotational sensor indicative of counts from first to last one for a total number of counts that is used for determining total angular displacement. The controller may be configured to receive data indicative of the angular movement of the dose setting member that can be used to determine from the outputs the amount of dose delivered by operation of the medication delivery device. The controller may be configured to determine from the outputs the amount of dose delivered by operation of the medication delivery device. The controller may include conventional components such as a processor, power supply, memory, microcontrollers, etc. Alternatively, at least some components may be provided separately, such as by means of a computer, smart phone or other device. Means are then provided to operably connect the external controller components with the sensor system at appropriate times, such as by a wired or wireless connection.

Figure 5:
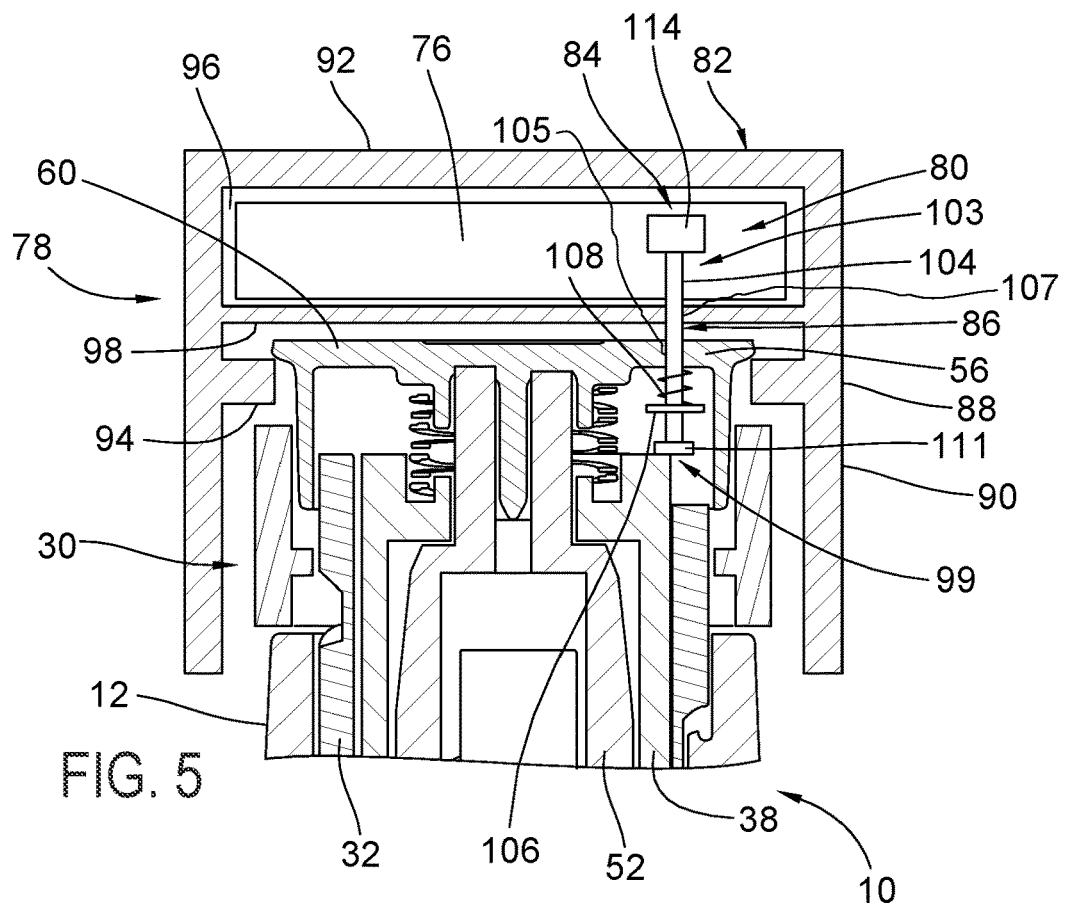
FIG. 5 is a side, diagrammatic view, partially in cross section, of an exemplary embodiment of a dose detection system shown attached to the proximal portion of a medication delivery device.

An exemplary electronics assembly 76 is shown in FIG. 5 and can include a flexible printed circuit board (FPCB) having a plurality of electronic components. The electronics assembly comprises a sensor system including one or more sensors operatively communicating with a processor for receiving signals from the sensor representative of the sensed rotation. Circuit board of electronics assembly 76 further includes a microcontroller unit (MCU) as the controller comprising at least one processing core and internal memory. The system includes a battery, illustratively a coin cell battery, for powering the components. The controller of electronics assembly 76 includes control logic operative to perform the operations described herein, including detecting the angular movement of the dose setting components during dose setting and/or dose delivery and/or detecting a dose delivered by medication delivery device 10 based on a detected rotation of the dose setting member relative to the actuator. Many of the components of the electronics assembly may be contained in a compartment 78 located proximal of the dose button 56.

The controller of electronics assembly 76 is operative to store the total angular movement used for determining dose delivery and/or the detected dose delivery in local memory (e.g., internal flash memory or on-board EEPROM). The controller is further operative to wirelessly transmit a signal representative of the total counts, total angular movement, and/or detected dose to a paired remote electronic device, such as a user's smartphone. Transmission may, for example, be over a Bluetooth low energy (BLE) or other suitable short or long range wireless communication protocol. Illustratively, the BLE control logic and controller are integrated on the same circuit.

The dose detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable, such as, for example, 9, 10, 15, 20, 24 or 36 degrees may be used for a unit or 0.5 unit. The sensor system is operable to determine the total angular displacement of a dose setting member during dose delivery. Thus, if the angular displacement is 90°, then 5 units of dose have been delivered.

The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device.

The sensor system components may be permanently or removably attached to the medication delivery device. In an illustrative embodiment, as least some of the dose detection system components are provided in the form of a module that is removably attached to the medication delivery device. This has the advantage of making these sensor components available for use on more than one pen injector.

The sensor system detects during dose delivery the relative rotation of the sensed component, and therefore of the dose setting member, from which is determined the amount of a dose delivered by the medication delivery device. In an illustrative embodiment, a rotational sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery. In some of the embodiments described herein, the sensed component includes a ring structure having a plurality of proximally extending projections circumferentially disposed relative to one another. Projections are shaped and sized to deflect a movable element of the rotational sensor. Embodiments described herein may be provided for a module that is removably attachable to the dose button of the delivery device or integrated within the dose button of the delivery device, with an embodiment illustrated in FIG. 10-11.

Referring to FIG. 5, there is shown in diagrammatic form a dose delivery detection system 80 including a module 82 useful in combination with a medication delivery device, such as device 10. Module 82 carries a sensor system, shown generally at 84, including a rotational sensor 86 and other associated components such as a processor, memory, battery, etc. Module 82 is provided as a separate component which may be removably attached to the actuator.

Dose detection module 82 includes a body 88 attached to dose button 56. Body 88 illustratively includes a cylindrical side wall 90 and a top wall 92, spanning over and sealing side wall 90. By way of example, in FIG. 5 side wall 90 is diagrammatically shown having inwardly-extending tabs 94 attaching module 82 to dose button 56. Module 82 is thereby attached to dose button 56 such that pressing on the module delivers a set dose.

Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In the illustrative embodiment, module 82 is rotationally fixed with dose button 56 and does not rotate during dose delivery. This may be provided structurally, such as with tabs 94 of FIG. 5, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides a compartment 78 containing some or all of electronics assembly 76. Compartment 78 defines a chamber 96 and may be open at the bottom, or may be enclosed, such as by a bottom wall 98. Bottom wall 98 may be positioned to bear directly against face 60 of dose button 56. Alternatively, bottom wall 98 if present may be spaced apart from dose button 56 and other contacts between module 82 and dose button 56 may be used such that an axial force applied to module 82 is transferred to dose button 56.

Further disclosed herein is a dose detection system operable to determine the amount of dose delivered based on relative rotation between a dose setting member and the device body. The dose detection system utilizes a dose setting member attached to the device body and rotatable relative to the device body about an axis of rotation during dose delivery. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

The dose detection system comprises a sensor system including a rotational sensor attached to the actuator. The sensed element includes surface features radially-spaced about the axis of rotation of the dose setting member. The surface features may be arranged to correlate to the equivalent of one unit of dose, although other angular relationships are also suitable, such as, for example, 9, 10, 15, 18, 20, 24 or 36 degrees may be used for a unit or 0.5 unit. The rotational sensor includes a movable element attached to the actuator and having a contact portion capable of resting against and spring-biased in the direction of the surface features of the sensed element. The contact surface is thereby positioned to move over the surface features during rotation of the sensed element relative to the actuator during dose delivery. The rotational sensor is responsive to the movement of the contact portion over the surface features and generates signals corresponding to the rotation of the dose setting member. A controller is responsive to the signals generated by the rotational sensor to determine a dose count for determining the amount of dose delivery based on the detected rotation of the dose setting member relative to the actuator during dose delivery.

The surface features may comprise anything detectable by the rotational sensor. As previously indicated, sensor systems may be based on a variety of sensed characteristics, including tactile, optical, electrical and magnetic properties, for example. In one aspect, the surface features are physical features which allow for detection of incremental movements as the dose setting member rotates relative to the actuator.

The contact surface is biased against the physical features to ensure proper contact between the contact surface and the physical features during rotation. In one embodiment, the movable element is a resilient member having one portion attached to the actuator at a location displaced from the contact surface. In one example, the movable element is a following member comprising a beam attached at one end to the actuator and having the contact surface at the other end. The beam is flexed to urge the contact surface in the direction of the surface features. Alternatively, the movable element may be biased in any of a variety of other ways. In addition to the use of a resilient beam, the biasing may be provided, for example, by use of a spring component. Such spring component may for example comprise a compression, tension, or torsion coil spring. In yet other embodiments, the movable element may be biased against the surface features of the sensed element by a separate resilient member or spring component bearing against the movable element.

In one embodiment, the surface features are uniform elements which are spaced intermittently around the axis of rotation of the sensed element. In a particular aspect, the surface features are equi-radially spaced projections separated by intervening recesses. The contact surface of the movable element is positioned to ride over the projections, and to move inwardly relative to the intervening recesses. The movable element may, for example, be a resilient beam which flexes outwardly along the projections, or a translating member which rides up over the projections.

In one aspect, the projections are ramped upward in the direction opposite to rotation of the sensed element during dose delivery to facilitate movement of the contact surface along and over the projections. In another aspect, the projections are provided with differing profiles in opposed angular directions to provide for detecting the direction of rotation of the sensed element relative to the actuator. The projections may extend in any direction detectable by the movable element. For example, the projections may extend axially or radially. Axial projections may extend proximally or distally. Radial projections may extend inwardly or outwardly.

The sensed element is attached to the dose setting member. Depending on the medication delivery device, the sensed element may be attached to the skirt, the flange or the dose dial, or any other component that rotates relative to the device body during dose delivery in relation to the amount of dose delivered.

In one aspect, the sensing system of dose detection system 80 is originally incorporated into a medication delivery device as an integrated system. In another aspect, there is disclosed a modular form of the dose detection system. The use of a removably attached module is particularly adapted to use with a medication delivery device in which the actuator and/or the dose setting member include portions external to the medication device housing. These external portions allow for direct attachment of the module to the actuator, such as a dose button, and/or attachment of a sensed element to a dose setting member, such as a skirt, flange, or dose dial member, as described herein. Alternately, the sensed element is integral with the medication delivery device and the module is removably attached. This has the advantage that the more complex and expensive electronics, including the rotational sensor and controller, may be reused with different medication deliver devices. By comparison, the sensed element may use relatively simple features, for example radially-spaced projections, which do not add significantly to the cost of the medication delivery device.

An exemplary medication delivery device incorporating an exemplary dose detection system is shown in FIGS. 5-9. The device includes a sensor system which detects surface features of a sensed element extending from one or more of the components of dose setting device 30, such as the dose dial member 32 and/or flange 38. In particular, sensor system 84 of dose detection system 80 includes the rotational sensor 86 and a sensed element 99 having surface features. Examples of the location and arrangement of the surface features are shown in illustrative examples: axial surface features of the flange (for example, FIG. 6), axial surface features of the dose dial member (for example, FIG. 10), outer radial surface features of the dose dial member (for example, FIG. 20), and inner radial surface feature of the flange (for example, FIG. 23).

Figure 6:
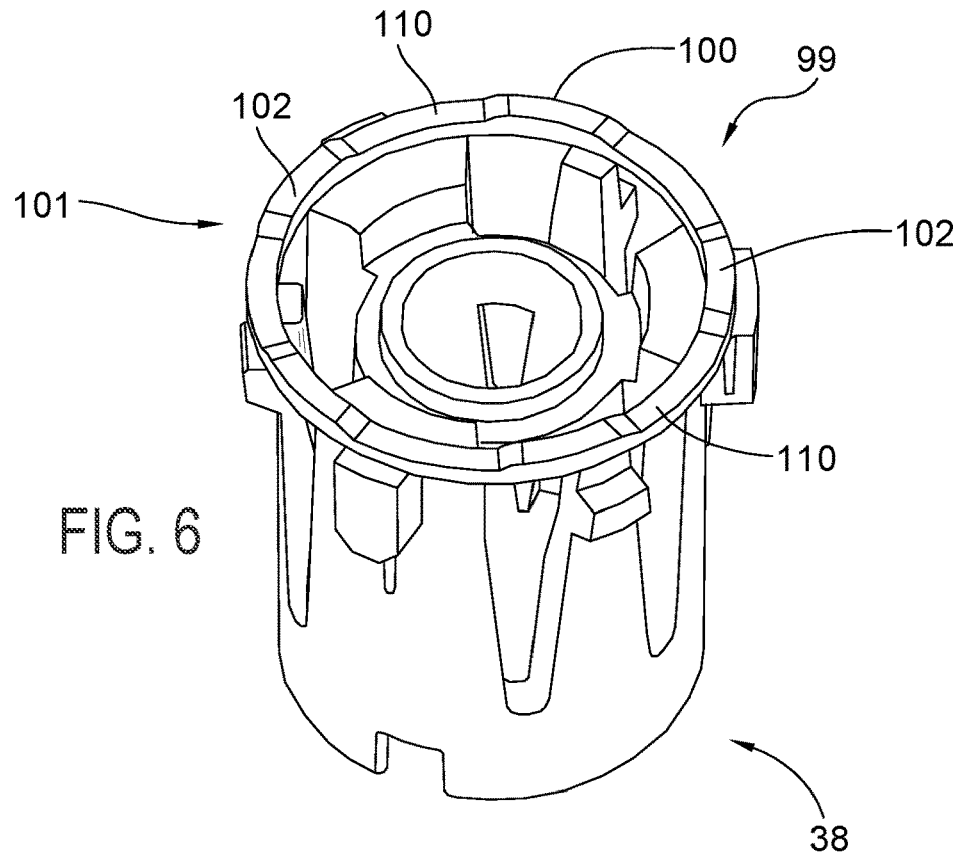
FIG. 6 is a perspective view of a flange including a sensed element.

In one example, shown in FIG. 6, sensed element 99 includes a ring 100 coupled to flange 38. It will be appreciated that ring 100 may be permanently affixed to flange 38 (shown) or dose dial member 32 with an adhesives and/or fasteners, or it may be configured to be removably attached to flange 38 or dose dial member, such as, for example, with a mechanical fastener or a carrier component. The ring may be omitted and the surface features may be integrally formed from flange 38 or does dial member 32 as a unitary member (shown for example in FIG. 17 or 23), such as, for example, through molding or additive manufacturing.

Figure 7:
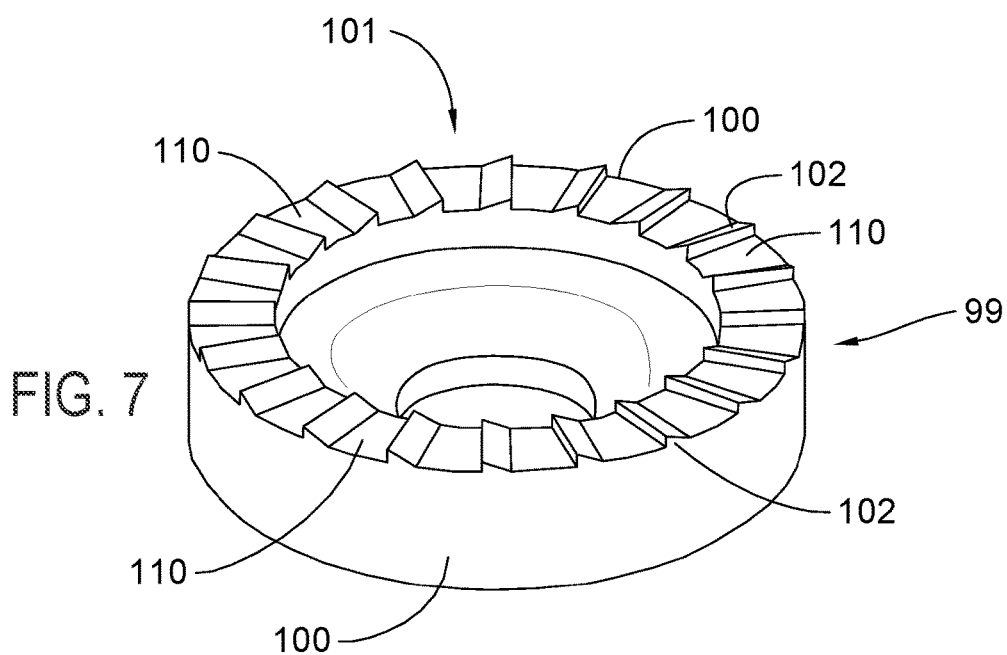
FIG. 7 is a perspective view of an embodiment of a sensed element.

As shown in FIGS. 6 and 7, surface features 101 comprising a series of ramp-like projections 102. Rotational sensor 86 includes one or more movable elements 103 (FIG. 5), in this instance comprising a following member pin 104 which is received through a button aperture 105 defined by the face 60 of dose button 56 and is positioned to have a distal contact surface 111 that is capable of resting against surface features shown as projections 102 as flange 38 rotates relative to dose button 56. Pin 104 is shown extending through a module aperture 107 defined by the distal bottom wall 98 that is in a coaxial alignment with button aperture 105. The interior surfaces that define the respective module aperture and button aperture may be configured to provide bearing support to the pin along two locations during its axial movement. Such size and arrangement of the apertures 105, 107 may enhance linear axial motion of the pin to reduce inconsistent readings from the sensor or switch employed. More than one pin and corresponding apertures defined by their respective component may be utilized for redundant sensing to reduce error readings.

Pin 104 may include a pin flange 106 received between contact surface 111 and dose button 56. Coil spring 108 is positioned between pin flange 106 and dose button 56 and biases pin 104 in the distal direction of projections 102. As flange 38 rotates during dose delivery, the pin(s) and dose button maintain their relative position, and contact surface 111 of pin 104 rides up over each surface feature shown as projection 102 against the biasing force of coil spring 108. Pin 104 then drops down into each recess 110 between adjacent projections. Pin 104 thereby operates as a following member which follows the contours of the projections and recesses.

Rotational sensor 86 further includes a sensing element 114 positioned to detect movement of pin 104 as it rides over projections 102 and falls into intervening recesses 110. The sensing element 114 may be provided in various forms operable to detect translational movement of pin 104. By way of example, the sensing element 114 is shown in FIG. 5 as comprising a microswitch that is operated to detect axial movement of pin 104 in the proximal direction each time pin 104 rides over a projection 102. This activation will result in successive on-off or off-on setting changes for the microswitch for each passage of a projection/recess pair of ring 100.

In the manner previously described, rotational sensor 86 detects angular movement of the dose setting member by counting the number of projections that trigger sensing element 114 during dose delivery. Rotational sensor 86 generates signals indicating this angular movement and those signals are used by the controller to determine the total rotation of the dose setting member during dose delivery that can be used to determine the amount of the dose delivery. In one example, the rotational sensor 86 generates signals indicative of a count number and the controller receives the generated signal. Controller may store the number of counts to an internal memory and/or transmit electronically the number of counts to an external device. Controller may compare the number of counts to an internal database that correlates the number of counts to a total angular movement and thus a dose delivered. The determined angular movement and/or dose delivered may be displayed on a local display or indicator system (such as numbers) as part of the electronics assembly and/or transmitted electronically to an external device.

Figure 8:
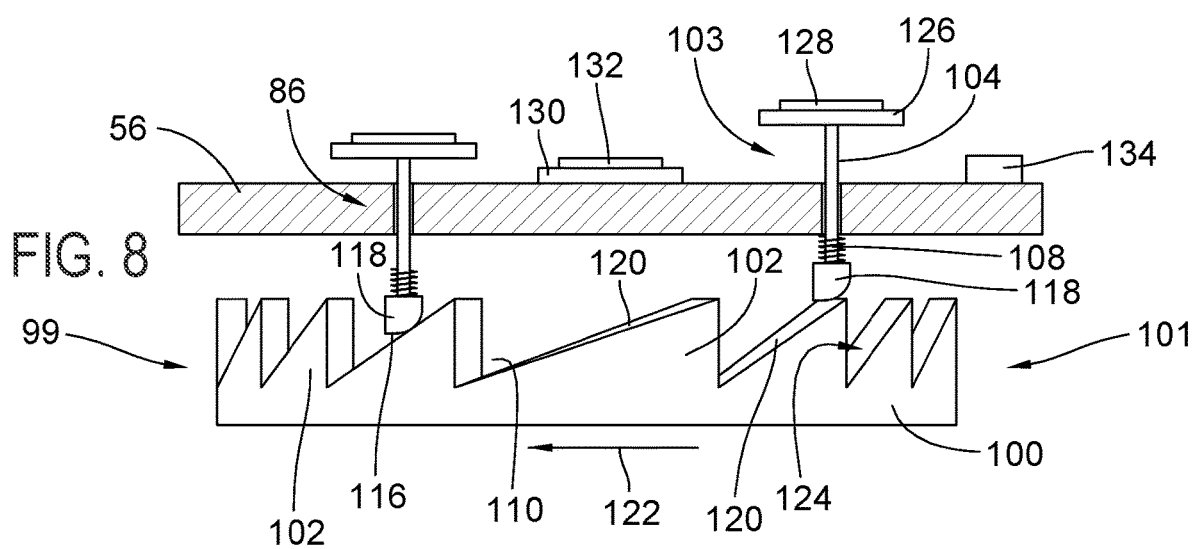
FIG. 8 is a diagrammatic view of other exemplary embodiments of the dose detection system.

FIG. 8 shows alternative dose detection systems which similarly use radially-spaced projections 102 and movable members 103 which comprise pins 104 which ride along the successive projections and recesses. As shown in FIG. 8, each movable member 103 includes a contact surface 116 which moves over the surface features 101 radially-spaced about the axis of rotation, e.g., projections 102. The contact surface 116 of pin 104 is shown in FIG. 8 as including an enlarged end portion 118 which may desirably be made of a durable, low-friction material which allows pin 104 to slide easily across projections 102. The enlarged end portion 118 having a cross-sectional area larger than the cross-sectional area of the pin. Also as shown in FIG. 8, projections 102 may be formed with a surface 120 which is ramped upward in the direction opposite to the direction of rotation, shown by arrow 122, of the dose setting member. This further facilitates movement of the following member over the projections.

In another aspect, the opposite side of projections 102 may be ramped to allow for rotation of the dose setting member in the opposite direction. Further, the two sides of the projections may be provided with different angles of inclination to allow the dose detection system to detect the direction of rotation. On the other hand, the opposite sides of the projections may be angled more steeply to prevent rotation in the other direction.

Described herein is an embodiment in which the actuator is moved distally relative to the device body to transition from a dose setting mode, or an at rest position, to a dose delivery mode. In the proximally displaced condition, the following members may be separated from the projections as one way to allow for rotation of the sensed element relative to the actuator in the direction opposite from dose delivery. However, as also described, in certain embodiments the actuator is rotationally fixed to the dose setting member during dose setting.

In FIG. 8 there is shown an alternative dose detection system which operates by detecting vibrations associated with rotation of the sensed element relative to the actuator during dose delivery. As sensed element 99 rotates in direction 122 relative to movable member 103, contact surface 116 forces pin 104 away from the dose setting member and against the biasing member, e.g., spring 108. Once the contact surface 116 passes over the top of the projection, the biasing member forces the following member quickly down into the subsequent recess 110. Referring to FIG. 8, with additional movement of sensed element 99 in the direction 122, spring 108 will drive pin 104 down into recess 124, where it will be stopped abruptly by contact with the bottom of the following recess 124. This abrupt stop will be accompanied by a vibration which is detected by the rotational sensor.

For example, in FIG. 8 there is shown a support 126 attached to the proximal end of pin 104 and carrying a rotation accelerometer 128. Rotation accelerometer 128 is provided primarily to detect vibrations indicative of rotation of the sensed element. In operation of the system, accelerometer 128 detects each vibration associated with the passage of pin 104 over the top of a projection and falling into the following recess. Accelerometer 128 may be of any type capable of detecting the vibration, and in a particular aspect comprises a 3-axes accelerometer. As used herein, this accelerometer is referred to as a "rotation accelerometer" to distinguish it as an accelerometer used in detecting rotation of the sensed element, rather than to suggest a particular type of accelerometer. Other sensors capable of detecting the rotation vibrations may also be used.

Also shown in FIG. 8 are optional sensor components including a second support 130 and a second accelerometer 132 that are useful in conjunction with rotation accelerometer 128. As used herein, the second accelerometer is referred to as a "background accelerometer" to distinguish it as an accelerometer used in detecting background vibrations, rather than to suggest a particular type of accelerometer. Background accelerometer 132 is provided primarily to detect background vibrations, such as caused by movement of the entire medication delivery device, which vibrations are not indicative of rotation of the sensed element. For this purpose, background accelerometer 132 is relatively isolated from pin 104, such as by pin 104 being slidingly received within an aperture in dose button 56.

Significant axial movement of pin 104 relative to dose button 56 will be sensed more strongly by rotation accelerometer 128 than by background accelerometer 132. If a vibration sensed by the rotation accelerometer is substantially the same as that sensed by the background accelerometer, then rotation of the sensed element will not be indicated. By comparison, if the amount of vibration detected by the rotation accelerometer is substantially greater than that detected by the background accelerometer at a given time, then rotation of the sensed element is indicated. The controller compares detected rotation vibrations and background vibrations to identify vibrations indicative of rotation of the sensed element relative to the actuator during dose delivery.

The action of the following member during rotation of the sensed element may also be associated with related sounds. In particular, a distinctive sound will be made by the impact of pin 104 against the bottom of recess 124. An alternative dose detection system utilizes this sound to detect rotation of sensed element 99 relative to dose button 56. By way of example, also shown in FIG. 8 is a microphone 134 forming a component of an alternative sensing system. Upon detecting a sound predetermined to be an indicator of rotation of the sensed element, the rotational sensor generates a signal identifying rotation of the sensed element associated with dose delivery. An additional background sound microphone may be used in order to be able to distinguish rotation sounds from other sounds.

Figure 9:
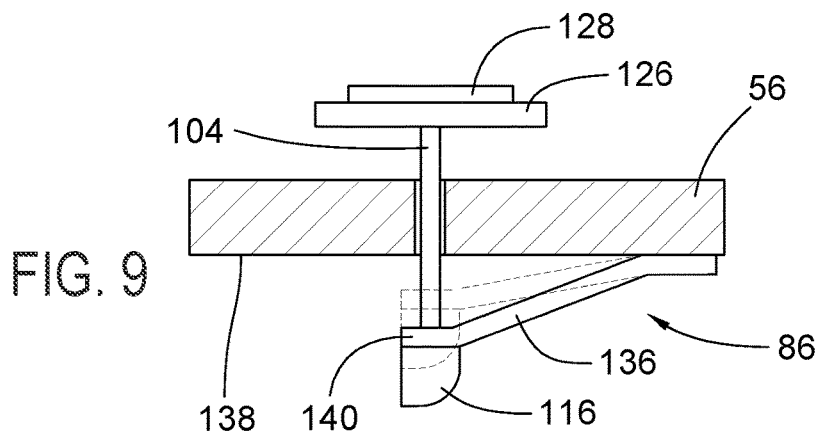
FIG. 9 is a diagrammatic view showing an alternate form of biasing member for the dose detection system.

As shown in FIG. 8, the following member may be biased, for example, by a coil spring. Alternatively, the following member may be biased against the surface features in various other ways. For example, a resilient member may be used to bias pin 104 against projections 102. As shown in FIG. 9, resilient member 136 is attached at one end to the underside 138 of dose button 56. Resilient member 136 includes a portion 140 at the opposite end resting against the enlarged end portion of the contact surface 116 of pin 104. Movement of contact surface 116 over the projections causes the pin to translate upwardly against the downward of resilient member 136, and contact surface 116 is thereby maintained in position against the surface features. Illustratively, in lieu of pin 104, the following member may comprise resilient member 136 and the contact surface may be positioned on end portion 140.

Referring now to FIGS. 1-2, there is shown a medication delivery device equipped with a sensing system that is described further as being used to determine the amount of a dose set by operation of the device. Such amount is determined based on the sensing of relative rotational movements during dose setting between members of the medication delivery device, where the sensed movements are correlated as applicable to the amount of the dose set. In different embodiments, the sensing system is configured to determine the amount of at least one of the dose set and the dose delivered by operation of the device, or alternatively both the amount of the dose set and the amount of the dose delivered by operation of the device.

Figure 10:
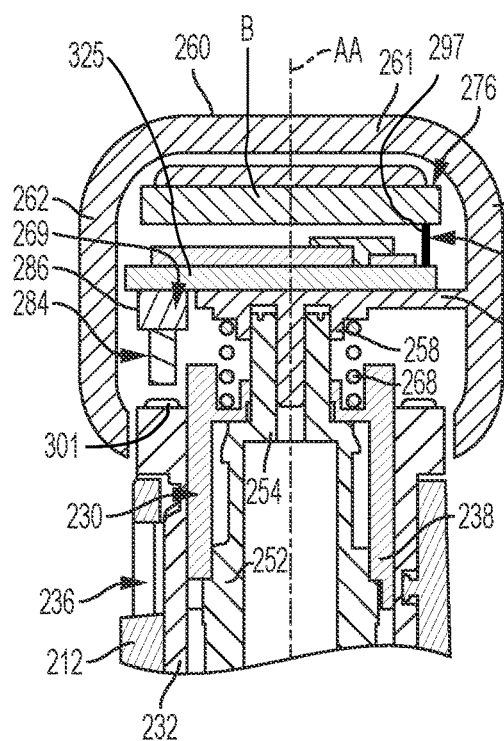
FIG. 10 is a side, diagrammatic view, partially in cross section, of a proximal portion of another embodiment of a medication delivery device with a dose detection system, with a dose button in a proximal position.
Figure 11:
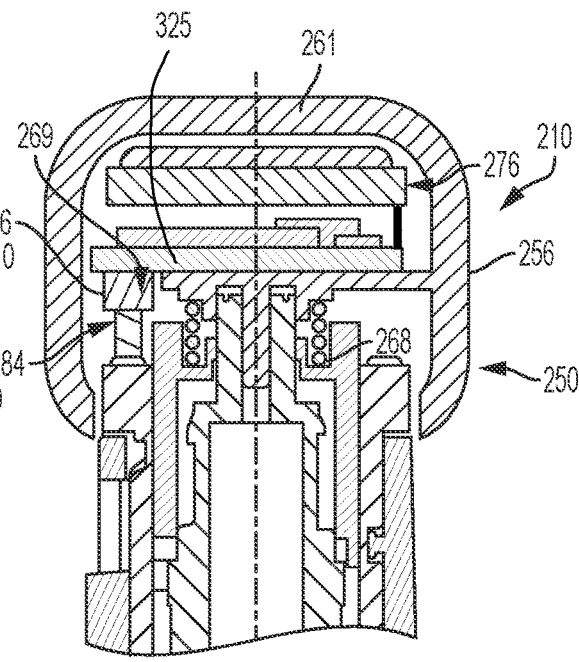
FIG. 11 is a side, diagrammatic view, partially in cross section, of the proximal portion of the medication delivery device in FIG. 10, with the dose button in a distal position.

FIGS. 10-11 illustrate the proximal portion of the device, now referenced as 210, with the dose detection sensor system 284 disposed within the dose button 256, rather than a module, and including the rotational sensor 286. The device 210 includes many of the same components operational for dose setting and dose dispensing as described with reference to the device 10, including at least a portion of the electronic components in the electronics assembly, and such components will have the same corresponding descriptions. Although the device 210 is shown as a device within an integrated dose detection sensing system, such sensing system may be incorporated in a module for removable attachment to a dose button.

The dose setting member 230 is coupled to the device housing 212 for setting a dose amount to be dispensed by device 210. Dose setting member 230 is operative to screw out in a proximal direction from housing 212 until it reaches a fully extended position corresponding to a maximum dose deliverable by device 210 in a single injection. The cylindrical dose dial member 232 of dose setting member 230 includes the helically threaded outer surface that engages the corresponding threaded inner surface of housing 212 to allow dose setting member 230 to spiral relative to housing 212. Dose dial member 232 includes the helically threaded inner surface that engages the threaded outer surface of the sleeve of the device 210, such as sleeve 34 in FIG. 2. The outer surface of dial member 232 includes dose indicator markings that are visible through the dosage window 236 to indicate to the user the set dose amount. Tubular flange 238 of dose setting member 230 is coupled in the open proximal end of dial member 232 and is axially and rotationally locked to dose dial member 232 by detents received within openings in dial member 232, such as, for example, shown in FIG. 2.

The actuator 250 of delivery device 210 includes the clutch 252 that is received within dose dial member 232. The proximal end of the clutch 252 includes the stem 254 that is axially extending from its proximal end. Dose button 256 of actuator 250 is positioned proximally of dose setting member 230, as shown. The mounting collar 258 of dose button 256 is attached to stem 254 of clutch 252, such as with an interference fit or an ultrasonic weld, so as to axially and rotatably fix together dose button 256 and clutch 252. The bias member 268, illustratively a spring, is disposed between the distal surface of mounting collar 258 of the dose button and the proximal surface of tubular flange 238 of the dose setting member to urge actuator 250 and dose setting member 230 axially away from each other. Dose button 256 is depressible by a user to initiate the dose dispensing operation. Bias member 268 biases the dose button 256 in the proximal first position (as shown in FIG. 10) where it stays during dose setting operation, until the user applies an axial force great enough to overcome the biasing force of member 268 to move the dose button 256 to the distal second position (as shown in FIG. 11) for dose dispensing operation.

Dose button 256 includes an upper proximal wall 261 with the disk-shaped proximal end surface 260 and the annular wall portion 262 extending distally from the proximal wall 261 to define a button housing cavity 265. Surface 260 of dose button 256 serves as the push surface against which a force can be applied manually, i.e., directly by the user to push actuator 250 in a distal direction. Dose button 256 include a distal wall 263 axially spaced from the proximal wall 261. Distal wall 263 may at least partially divide the cavity 265 into two proximal and distal cavity portions. The mounting collar 258 of dose button 256 is shown extending distally from an intermediate location of the distal wall 263 for attachment with stem 254 of clutch 252. In one example, the surface features 301 are disposed within the cavity 265 radially outside bias member 268. As shown, the rotational sensor and the controller are disposed within the cavity 265.

Distal wall 263 may be configured to allow a portion of the sensor system to extend distally beyond the distal wall 263. Distal wall 263 may include a discrete opening or may extend partially across the cavity 265 from a portion of the annular wall portion 262 to stop short of the opposite end of annular wall portion to define an axial aperture 269, as shown in FIGS. 10-11. The axial aperture 269 may be spaced radially from the axis AA toward the outer end so that the rotational sensor that extends through the aperture 269 is placed over the surface features 301 that are radially-spaced about the axis AA of rotation. The electronics assembly 276 is shown housed within the dose button 256. The circuit board 325 includes a plurality of electronic components, and is shown mounted on the proximal face of the distal wall 263. The sensor system 284 includes the rotational sensor 286 operatively communicating with the processor of the controller of the circuit board for receiving signals from the sensor representative of the sensed rotation. The rotational sensor 286 is shown mounted to a distal face of the circuit board. The controller of the electronics assembly 276 includes at least one processing core in electric communication with the rotational sensor 286 and internal memory. The assembly 276 includes a battery B, illustratively a coin cell battery, for powering the electronics components. The controller includes control logic operative to perform the operations described herein, including detecting a dose delivered by the medication delivery device based on a detected rotation of the dose setting member relative to the actuator. Some of the components in the electronics assembly 276 are shown as unconnected for illustrative purposes only, and are actually electrically connected to one another, such as by connectors, wires, or conduits, as understood in the art, such as shown by 297 in FIG. 10, and illustrated in other figures.

Figure 14:
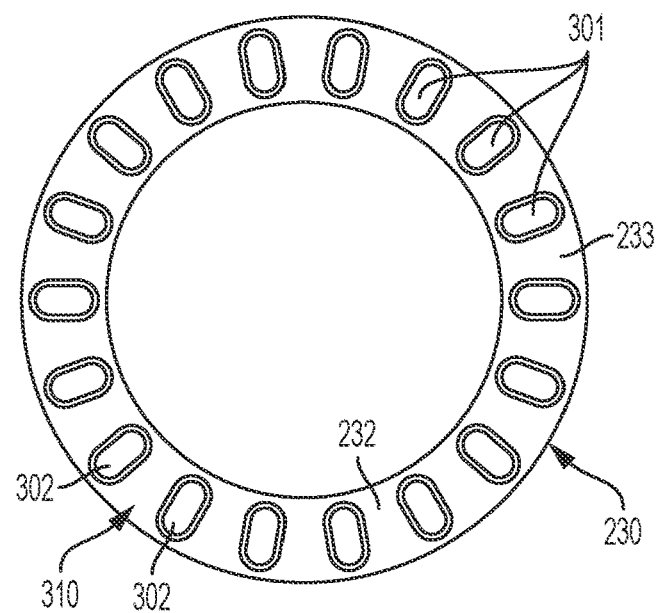
FIG. 14 is an axial top view of a dose setting member, depicting an example of surface features.

Sensor system 284 with the rotational sensor 286 is configured to detect surface features 301 extending from one or more of the components of dose setting device 230, such as the dose dial member 232 (as shown) and/or flange 238. For example, with reference to FIG. 14, the axial end surface 233 of the dose dial member 232 of the dose setting device 230 in the shape of a ring may define surface features 301, shown as projections 302 spaced radially from one another along the axial end surface, projections separated by intervening recesses 310. In the example shown, there are eighteen projections, each spaced twenty degrees apart from adjacent ones.

The dose button 256 is movable relative to device housing 212 between two positions. In FIG. 10, the dose button 256 is in the proximal position where the device is in a first operating dose setting mode in which the dose button may be used to set a dose. In FIG. 11, the dose button 256 is in the distal position where the device is in a second operating dose delivery mode in which the dose button may be used to deliver the dose. In certain embodiments, the dose button 256 is rotationally fixed to the dose setting member in the dose setting mode, and dose button 256 may be rotated to set a dose. In this position, rotational sensor 286 is axially displaced from the surface features 301. In the dose setting mode, the rotational sensor 286 may remain inoperable and the electronics assembly may remain powered off or in a low power state.

Upon pressing proximal wall 261, dose button 256 advances distally relative to housing 212, compressing spring 268, as shown in FIG. 11. Continued pressing of the dose button 256 distally results in back driving dose dial 232 in a spiral direction relative to housing 212. As a result, the dose dial 232 and flange 238 is driven to rotate by the axially moving dose button. The dose detection system may only be operable for counting when the dose button is being pressed. The electronics assembly may include a clock or timer to determine the time elapsed between counts caused by trigger of the rotational sensor from the surface features of the sensed element. When trigger arm is not activated, that is, no counts detected by the controller, for a period of time, this may be used to indicate that the dose is completed.

Upon the sensing of the initial one of surface features 301, the controller is configured to allow wake-up or activation of the electronics assembly 276 to a greater or full power state. Triggering of wake-up feature is configured to allow power transmission from the power source (shown as battery) for powering up the electronic components for dose sensing in order to minimize inadvertent power loss or usage when a dose dispensing event is not occurring. In other embodiments, a separate wake-up switch may be provided and arranged within the dose button housing and triggered when the dose button 256 is in its distal position. In this instance, the wake-up switch may be located, for example, along the upper end of the flange. After activation of the electronics assembly, the controller begins receiving generated signals from the rotational sensor indicative of counts from first to last one for a total number of counts that is used for determining total angular displacement and thus the amount of dose delivered.

Figure 12:
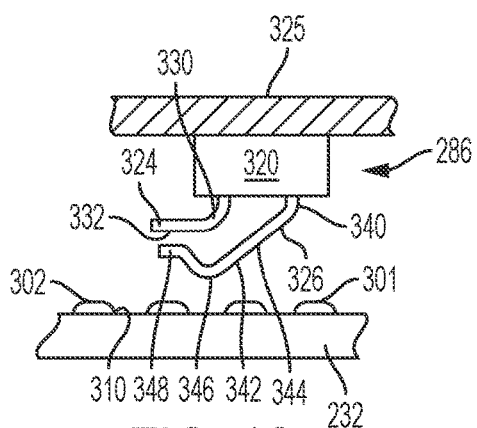
FIG. 12 is a side magnified view of an example of a rotational sensor provided in the medication delivery device in FIG. 10, with the dose button in the proximal position.
Figure 13:
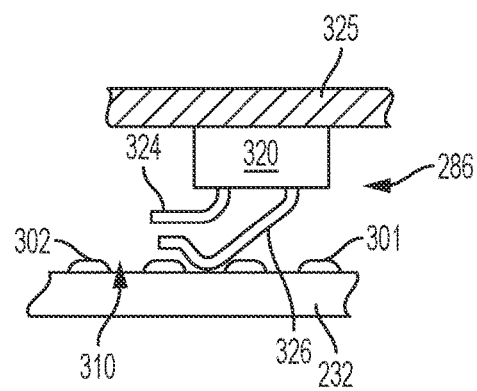
FIG. 13 is a side magnified view of the rotational sensor in FIG. 12, with the dose button in the distal position.

FIGS. 12-13 depict one example of the rotational sensor 286 provided in the device 210. For example, the rotational sensor 286 includes a sensor body 320 and a movable element comprising a pair of contacts 324, 326. The contacts 324, 326 may be resilient, that is having a natural configuration in one state, and capable of being moved or deflected to another state when under a force and returning to the natural configuration when the force is removed. The sensor body 320 is shown mounted to the circuit board 325 and is operably coupled to the controller of electronics assembly, and is configured to transmit a sensor signal of an electronic characteristic (voltage, resistance, current signal) defined by the contacting or separation of the contacts 324, 326 to the controller. The contacts 324, 326 may remain spaced apart in a natural state until brought together in contact with one another in an operational state by deflection of at least one of the contacts (shown as contact 326) during engagement with the surface features 301. Alternatively, both of contacts 324, 326 may be configured to deflect upon engagement with surface features and contact one another due to the deflection. After engagement of contact 326 with the surface feature 301, the contact 326 may return to the natural state where it is in spaced relationship with contact 324. Alternatively, the contacts 324, 326 may remain contacting each other in a natural state and configured to separate from a contacting relationship due to engagement with the surface features 301, and return to the natural state in their contacting relationship after the passage of the surface feature. According to FIG. 12, the rotational sensor 286 is in the proximal position as the dose button 256 is in its proximal position where the device is in its first operating dose setting mode. According FIG. 13, the rotational sensor 286 is in the distal position as the dose button 256 is in its distal position where the device is in its second operating dose delivery mode.

FIGS. 12-13 illustrate an example configuration of the contacts 324, 326, although other configurations of the contacts may be utilized. The first contact 324 is shown extending axially from the sensor body 320. The first contact 324 includes a first segment 330 coupled to the sensor body 320 and a second segment 332 extending from the first segment 330. The first segment 330 is shown extending axially from the sensor body 320, and the second segment 332 is shown extending radially from the first segment 330 at an elbow connection. The second contact 326 includes a first segment 340 coupled to the sensor body 320 and a second segment 342 extending from the first segment 340. The first segment 340 is shown extending axially from the sensor body 320. The second segment 342 is shown extending generally radially from the first segment 340 at an elbow connection. The second segment 342 includes an arm portion 344, a transition engagement portion 346, and a tip contact portion 348 coupled in sequence from the first segment 340. The arm portion 344 is sized and shaped to place the tip contact portion 348 underneath the second segment 332 of the first contact. The arm portion 344 is shown extending at an incline in the axial and radial directions from the first segment 342. The transition engagement portion 346 is configured to engage directly the surface feature 301. The transition engagement portion 346 may have a U-shape, V-shape, or ramped shape to transition the second segment 342 from the distal direction to the proximal direction. The tip contact portion 348 extends in the radial direction and may be generally in parallel and spaced apart with respect to the second segment 332 of the first contact 324 in the natural state. The shape of the transition engagement portion 346 may allow for sliding contact along the surface features 301 without causing jamming of the rotating dose dial member. The depth of the shape of the transition engagement portion 346 is sized such that upon its distal surface engaging the surface features 301, the second contact 326 defects in the proximal direction at the elbow with the first segment to place the proximal surface of the tip contact portion 348 in contact with the distal surface of the second segment 332 of the first contact 324. Such contact is sufficient to generate a sensor signal of an electronic characteristic. Alternatively, one of the contacts may be employed, such as contact 326 and the surface features may have an electrical conductive property, such as being coated with a metallic material, such that upon engagement between the contact and the surface feature the rotational sensor can generate a signal, as described herein.

Figure 15:
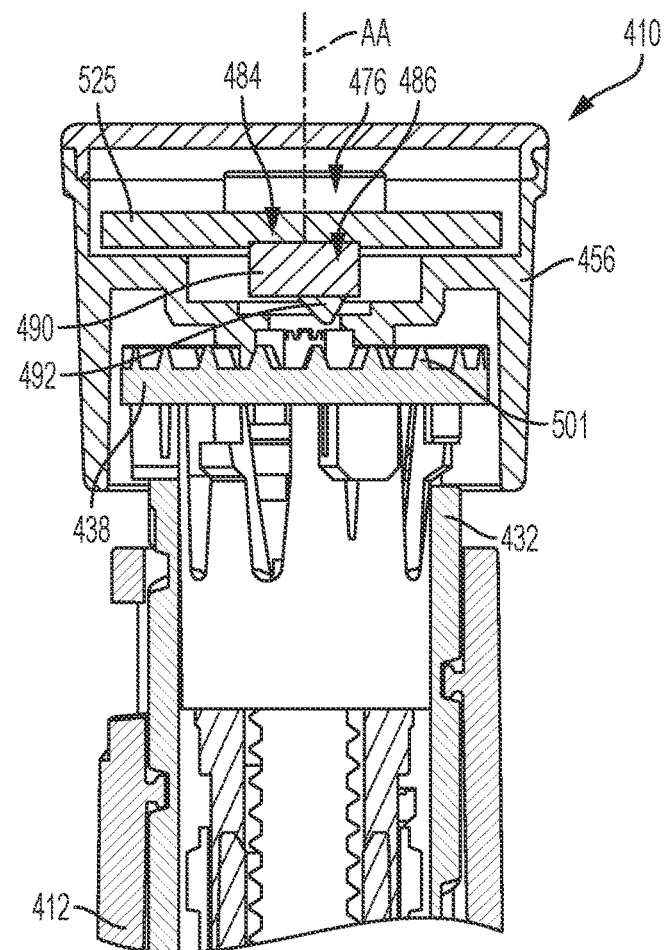
FIG. 15 is a side, diagrammatic view, partially in cross section, of a proximal portion of another embodiment of a medication delivery device with a dose detection system, with its dose button in a proximal position.
Figure 16:
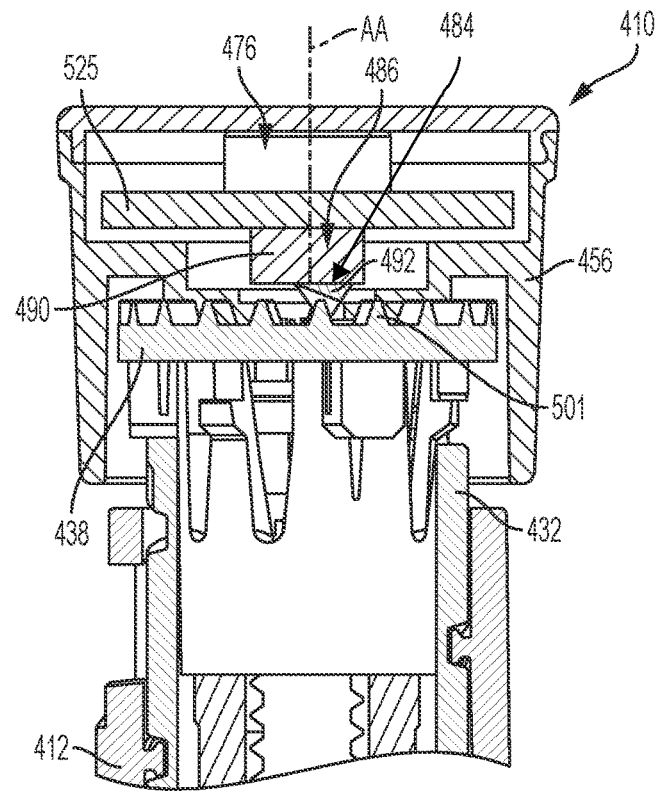
FIG. 16 is a side, diagrammatic view, partially in cross section, of the proximal portion of the medication delivery device in FIG. 15, with the dose button in a distal position.

FIGS. 15-16 depict the proximal portion of the device, now referenced as 410. The device 410 includes many of the same components operational for dose setting and dose dispensing as described with reference to the device 10 or 210, including at least a portion of the electronic components in the electronics assembly for the dose detection system, and such components will have the same corresponding descriptions. Although the device 410 is shown as a device within an integrated sensing system, such sensing system may be incorporated in a module for removable attachment to a dose button. The device 410 may have the same device components as device 210, such as, for example, device housing 412, dose dial member 432, flange 438, and electronics assembly 476, except with respect to a different rotational sensor configuration and a different dose setting member with the surface features used for sensing, as will be described. As shown, the rotational sensor and the controller are disposed within the cavity of the button.

Another example of the rotational sensor, referenced generally as 486, of the dose detection sensor system 484 that can be used with any module and/or device described herein. For example, the rotational sensor 486 is a microswitch including a sensor body 490 and a movable element comprising a trigger arm 492. With reference to the previous figures, the dose button housing is configured to include the axial aperture spaced radially from the axis AA toward the outer end in order for trigger arm 492 of the rotational sensor 486 to extend through for placement over the surface features 501 that are radially-spaced about the axis AA of rotation. The trigger arm 492 is biased by an internal spring into a natural state until being overcome by a force to urge the trigger arm 492 into a position away from the natural state position to an operational state. The sensor body 490 is mounted to the circuit board 525 and is operably coupled to the controller of electronics assembly, and is configured to transmit a sensor signal of an electronic characteristic (voltage, resistance, current signal) defined by the trigger arms movement to the controller. The trigger arm 492 may remain in the natural state until brought into engagement with the surface features 501. After engagement between trigger arm 492 with the surface feature 501, the trigger arm 492 may return to the natural state. According to FIG. 15, the rotational sensor 486 is in the proximal position as the dose button 456 can be biased in its proximal position where the device 410 is in its first operating dose setting mode. The bias member (not shown) may be axially disposed between the dose button and the dose setting member, and the surface features 501 are disposed radially outside the bias member, such as shown in FIGS. 10-11. According FIG. 16, the rotational sensor 486 is in the distal position as the dose button 456 is in its distal position where the device is in its second operating dose delivery mode.

Figure 17:
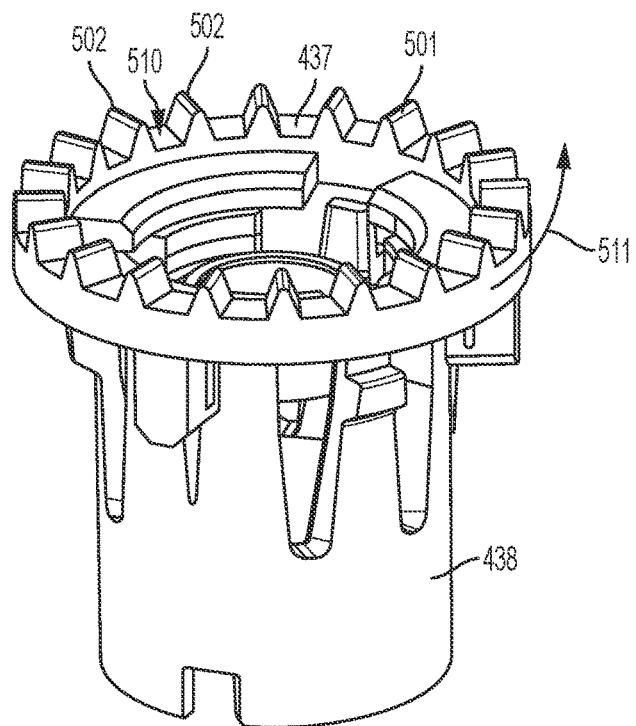
FIG. 17 is a perspective view of an example of a flange with another example of surface features along an axial surface.

FIG. 17 shows one example of a dose setting member having the surface features 501. In one example, the axial surface 437 of the proximal end of the flange 438 may be integrally defined with the surface features, shown as projections 502 with intervening recesses 510, such as a molded part or part made with additive manufacturing. In another example, a ring component with the surface features defined along one of its surfaces may be coupled to the axial surface of the flange. It will be appreciated that ring may be permanently or temporarily affixed to flange with an adhesives and/or fasteners. In another example, the surface features are formed or otherwise coupled to the dose dial member.

As shown in FIGS. 15-17, surface features 501 includes a series of projections 502 each having a ramp-like shape. Projections 502 may be formed with a surface which is ramped upward in the direction opposite to the direction of rotation, shown by arrow 511, of the flange 438. This further facilitates movement of the trigger arm 492 over the projections 502. In another aspect, the opposite side of projections 502 may be ramped to allow for rotation of the dose setting member in the opposite direction. Further, the two sides of the projections 502 may be provided with different angles of inclination to allow the dose detection system to detect the direction of rotation. On the other hand, the opposite sides of the projections 502 may be angled more steeply to prevent rotation in the other direction.

The following embodiments illustrate different arrangements of the rotational sensor and surface features along a radial direction. FIGS. 18-21 illustrates the proximal portion of the device, now referenced as 610, depicting the rotational sensor of the dose detection system positioned radially outward relative to surface features that extend radially outward. The device 610 includes many of the same components operational for dose setting and dose dispensing as described with reference to the device 10, 210, or 410, including at least a portion of the electronic components in the electronics assembly for the dose detection system, and such components will have the same corresponding descriptions. Although the device 610 is shown as a device within an integrated sensing system, such sensing system may be incorporated in a module for removable attachment to a dose button. Although the rotational sensor is shown as a microswitch that is similar to what is shown in FIG. 15, the rotational sensor can be any of sensors described herein. The device 610 may have the same device components as device 210, such as, for example, device housing 612, dose dial member 632, flange 638, and electronics assembly 676, except with respect to a different rotational sensor configuration and a different dose setting member with the surface features used for sensing, as will be described.

The rotational sensor 686 of the sensor system 684 is shown disposed along the annular wall portion 662 of the of the dose button 656. The sensor body 690 of the rotational sensor 686 may be within an aperture 695 defined by the annular wall portion 662 or, in alternative embodiments, the sensor body 690 may be disposed along an interior surface of the wall portion 662. The movable element comprises the trigger arm 692 that extends radially inward toward the longitudinal axis AA. Although not shown, the rotational sensor 686 is operably coupled to the controller of the electronics assembly, such as, via electrical conductors connected between the sensor 686 and the circuit board that extend along the interior surface of the dose button housing.

The rotational sensor 686 is configured to transmit a sensor signal of an electronic characteristic (voltage, resistance, current signal) defined by movement of the trigger arm of the rotational sensor 686 to the controller.

Figure 19:
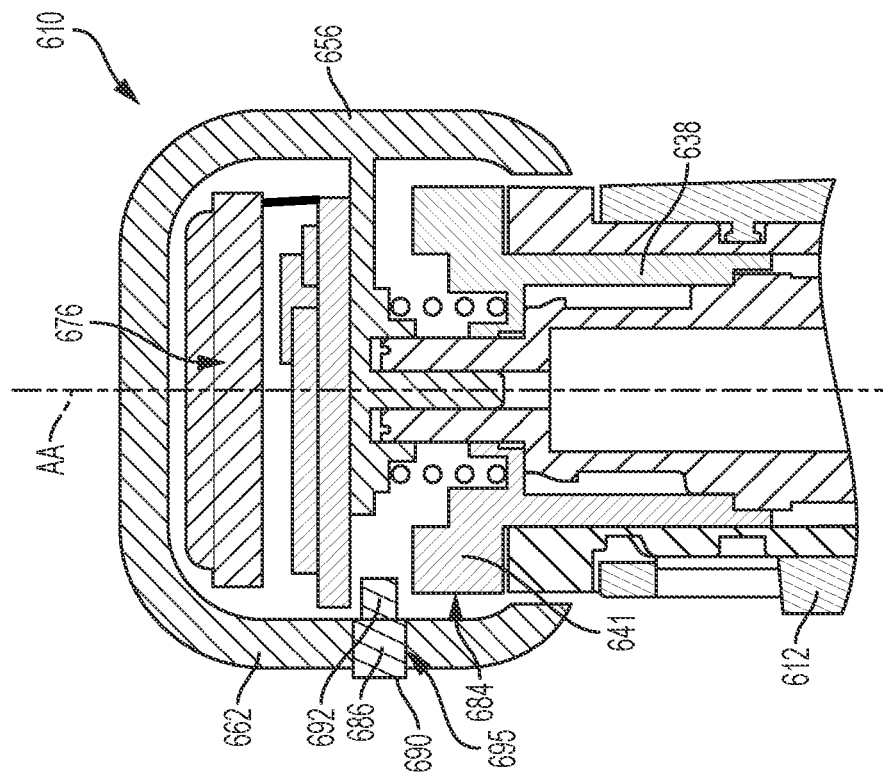
FIG. 19 is a side, diagrammatic view, partially in cross section, of the proximal portion of the medication delivery device in FIG. 18, with its dose button in a proximal position.
Figure 21:
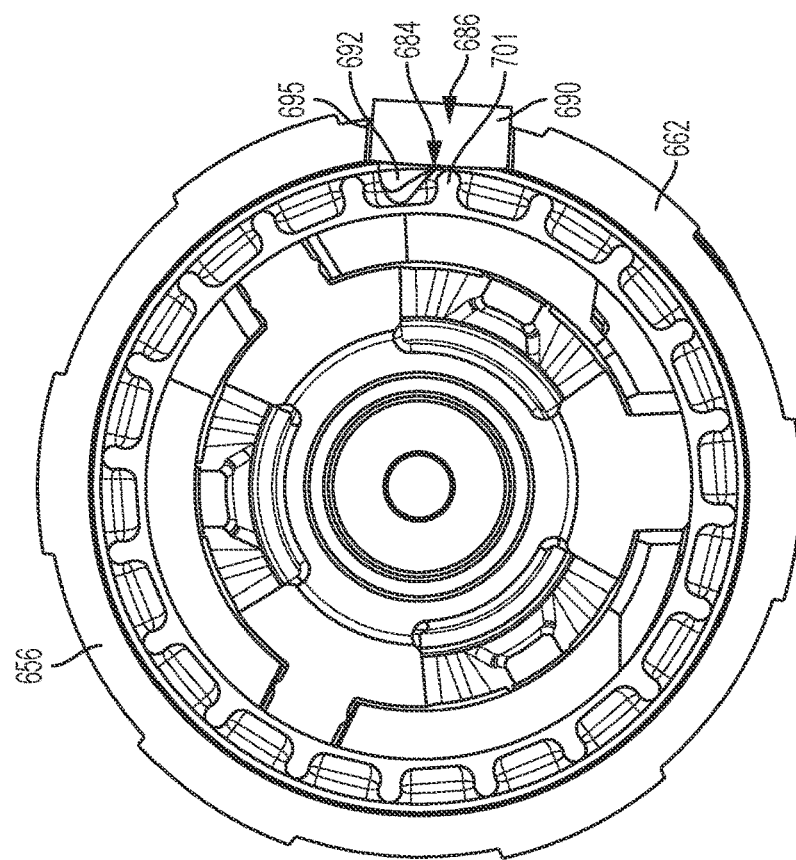
FIG. 21 is an axial top view of the proximal portion of the medication delivery device of FIG. 18, depicting the arrangement of a rotational sensor and the surface features.
Figure 20:
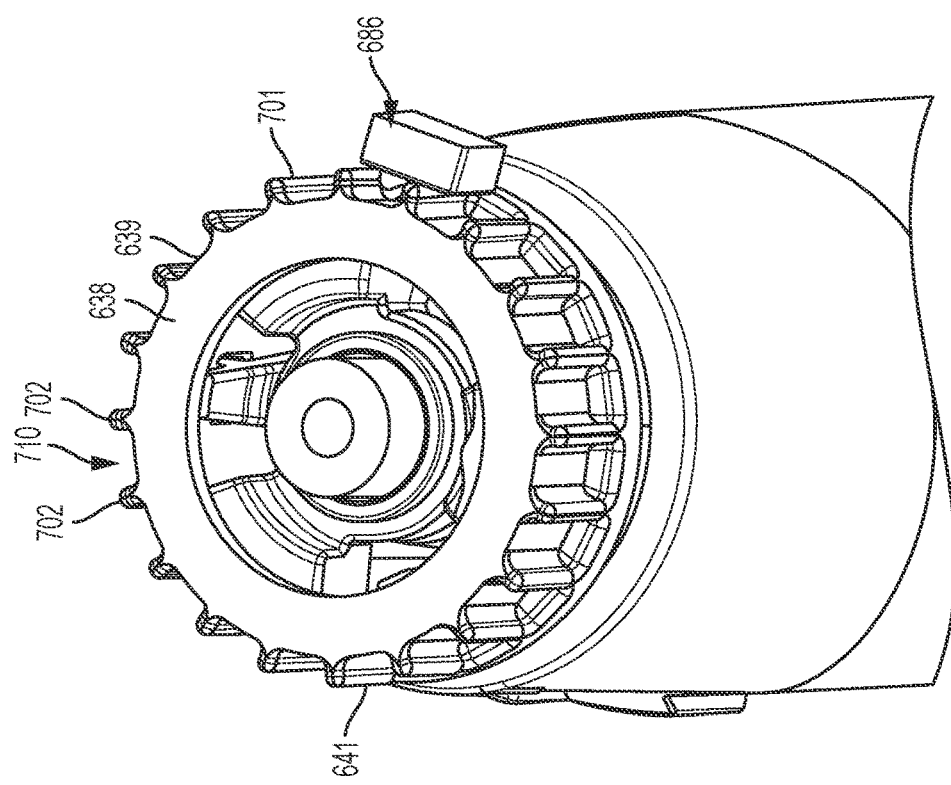
FIG. 20 is a perspective view of the proximal portion of the medication delivery device of FIG. 18, depicting the arrangement of a rotational sensor and the surface features.

FIGS. 19-21 show the flange having the surface features. In one example, the outer radial surface 639 of a proximal annular end 641 of the flange 638 may be integrally defined with the surface features 701 that radially-spaced about the axis of rotation, shown as radial projections 702 with intervening recesses 710, such as a molded part or part made with additive manufacturing. In another example, a ring component with the surface features 701 defined along the outer radial surfaces may be coupled to the axial surface of the flange. It will be appreciated that ring may be permanently or temporarily affixed to flange with an adhesives and/or fasteners. In another example, the surface features 701 are formed or otherwise coupled to the dose dial member. Surface features may include a series of ramp-like projections as described previously. The radial projections 702 may extend between a proximal end and a distal end to define axial ridges.

FIGS. 18-19 illustrate the rotational sensor in the proximal position as the dose button 656 is in its proximal position where the device 610 is in its first operating dose setting mode. The dose button 656 is movable to its distal position (with reference to FIGS. 20-21) to place the rotational sensor in the distal position where the device is in its second operating dose delivery mode. In one example, the trigger arm 692 may enter through one of the recesses 710 from the proximal end when the dose button is being moved to its distal position so that the trigger arm is engageable with the surface features. Controller is capable of counting the number of times the trigger arm moves between a first trigger and last trigger and such data is used for determining a dose delivery.

FIG. 22 illustrates the proximal portion of the device, now referenced as 810, depicting the rotational sensor positioned radially inward relative to surface features that extend radially inward. The device 810 includes many of the same components operational for dose setting and dose dispensing as described with reference to the device 10, 210, 410 or 610, including at least a portion of the electronic components in the electronics assembly for the dose detection system 844, and such components will have the same corresponding descriptions. Although the device 810 is shown as a device within an integrated sensing system, such sensing system may be incorporated in a module for removable attachment to a dose button. The device 810 may have the same device components as device 210, such as, for example, device housing 812, dose dial member 832, flange 838, dose button 856, and electronics assembly 876, except with respect to a different rotational sensor configuration and a different dose setting member with the surface features used for sensing, as will be described.

Like the arrangement of the rotational sensor 286, the rotational sensor 886 is shown extending from the distal face of the circuit board through the axial aperture 869. The sensor body of the rotational sensor 886 is mounted to the circuit board and is operably coupled to the controller of electronics assembly 876, and is configured to transmit a sensor signal of an electronic characteristic (voltage, resistance, current signal) defined by movement of the movable element that is comprised of the trigger arm of the rotational sensor 886 to the controller. The mounting of the rotational sensor 886 is arranged to place its trigger arm within periphery of a proximal annular end 841 of the flange 838 and facing radially outward for engagement with the surface features 901.

FIGS. 23-24 show the flange 838 having the surface features. In one example, the inner radial surface 839 of the proximal annular end 841 of the flange 838 may be integrally defined with the surface features 901 that are radially-spaced about the axis of rotation, shown as projections 902 with intervening recesses 910, such as a molded part or part made with additive manufacturing. In another example, a ring component with the surface features defined along the outer radial surfaces may be coupled to the axial surface of the flange. It will be appreciated that ring may be permanently or temporarily affixed to flange with an adhesives and/or fasteners. In another example, the surface features 901 are formed or otherwise coupled to the dose dial member. Surface features 901 may include a series of ramp-like projections. The surface features may extend between a proximal end and a distal end to define an axial ridge.

FIG. 25 illustrates the rotational sensor as a piezoelectric sensor 1000 that can be used with any of the devices 10, 210, 410, 610 or 810. The piezoelectric sensor 1000 may be oriented similarly to the rotational sensors described above, such as axial, radially outward or radially inward. In one example, the trigger arm 1002 of the piezoelectric sensor 1000 is defined as a film of piezoelectric material that is bendable. The film extends from the sensor body 1004, and the sensor body 1004 includes a first electrode 1006 and a second electrode 1008. The sensor body may include a polymer cast housing, such as, for example, fluoropolymer (e.g., polyvinylidene fluoride) or polyurethane. Piezoelectric sensor 1000 is a transducer that converts mechanical energy to electrical energy. More specifically, piezoelectric sensor 1000 converts mechanical deformation of the trigger arm 1002 to a proportional electrical signal (charge or voltage). Thus, when the trigger arm 1002 of piezoelectric sensor is subjected to a mechanical force and undergoes deformation or strain, piezoelectric sensor 1000 is configured to generate a proportional electrical signal between first electrode 1006 and second electrode 1008 for detection by an analog voltage detector of the electronics assembly. The mechanical deformation of trigger arm 1002 of piezoelectric sensor 1000 may be resilient, such that trigger arm 1002 is able to return to its original, natural shape when the force is removed.

Controller of the electronics assembly may be configured to receive an analog piezoelectric signal from the voltage detector of each piezoelectric sensor 1000, which may be a substantially ring-shaped signal. Controller of the electronics assembly may be programmed to convert the analog piezoelectric signal to a digital signal, such as, for example, an intermediate digital signal, which may be a high-frequency signal that represents the time of the "click" or deformation event. Controller of the electronics assembly may be further programmed to convert the intermediate digital signal to a conditioned digital signal, which may be a single step/square wave with a predetermined width W representing a predetermined time, as described further below.

A signal processing logic for use by control system. Logic subject the analog piezoelectric signal to a direct current (DC) voltage offset step using resistors, followed by an amplification step using amplifier, and followed by an analog-to-digital conversion step using comparator to generate the intermediate digital signal. The signal may be generated when the incoming voltage is at or above a predetermined voltage (e.g., 1.3 V). Alternatively, the signal may be ignored when the incoming voltage is less than the predetermined voltage. The intermediate digital signal may be converted to the conditioned digital signal by turning the signal "on" when initiating a timer at a timer initiation step and turning the signal "off" when the timer expires after a predetermined time at a timer expiration step. The timing steps may be performed using a resistance-capacitance (RC) timing loop. The predetermined time associated with the timing steps may control the width W of the conditioned digital signal and may be adjusted to match the time of each rotation and deformation event to minimize errors. Logic may output a number corresponding to the number of digital signals counted over a period of time.

The devices described herein, such as, for example, devices 210, 410, 610 or 810, may include the dose detection system involving detecting relative rotational movement between two members. With the extent of rotation having a known relationship to the amount of a delivered dose, the sensor system in any of the embodiments described herein operates to detect the amount of angular movement from the start of a dose injection to the end of the dose injection. The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device. Controller is configured to count the number of generated signals. The count may be transmitted electronically to an external device. External device described herein may refer to a server, mobile phone, or other known computer systems. The count may be correlated to an absolute rotational angle, which is then used by a processor of the external device to determine the amount of dose delivered. The signal generated by the initial contact of the contacts may be operable to wake-up or activate the controller, as previously described.

In the manner previously described, any of the rotational sensors described herein, such as rotational sensors 286, 486, 686, 886, detects angular movement of the dose setting member by counting the number of surface features that trigger activation of trigger arm during dose delivery. Each of rotational sensors generates signals indicating this angular movement and those generated signals are used by the controller of electronics assembly to determine the total number of counts or units. Such total number of counts have a corresponding total rotation of the dose setting member during dose delivery, and thereby the amount of the dose delivery. In one example, each of the rotational sensors generates signals indicative of a count number and the controller receives the generated signal. Controller may store the number of counts on-board in internal memory and/or transmit the number of counts to an external device. Controller may compare the number of counts to an on-board database that correlates number of counts to a total angular movement. The determined angular movement may be displayed on a local display and/or transmitted to an external device.

The devices described herein, such as, for example, devices 210, 410, 610 or 810, may include the wake-up feature described herein, where the depression of the dose button to its distal position during initial dose delivery can activate the controller. For example, upon the sensing of the initial one of surface features, the controller of electronics assembly is configured to allow wake-up or activate the electronics assembly to a full power state. Triggering of wake-up feature is configured to allow power transmission from the power source (shown as battery) for powering up the electronic components for dose sensing in order to minimize inadvertent power loss or usage when a dose dispensing event is not occurring. In other embodiments, a separate wake-up switch may be provided and arranged within the dose button housing of any one of the devices described herein and triggered when the dose button is in its distal position. In this instance, the wake-up switch may be located, for example, along the upper end of the flange.

In some embodiments, a single sensing system may be employed for both dose detection sensing and wake-up activation. For example, the devices described herein, such as, for example, devices 210, 410, 610 or 810, may having a controller configured to, upon the sensing of the initial first surface feature, allow wake-up or activation of the electronics assembly to a full power state. Subsequently, the controller is configured to, upon the sensing of the first surface feature (or second in order) after the initial first surface feature, count the total number of surface features until rotation of the dose setting member is stopped upon completion of the dose dispensing phase. One of the advantages of a single system with this abundant functionality is that may reduce the number of electronic components in the device as well as the manufacturing complexity with additional sensors.

The shown device is a reusable pen-shaped medication injection device, generally designated, which is manually handled by a user to selectively set a dose and then to inject that set dose. Injection devices of this type are well known, and the description of device is merely illustrative as the sensing system can be adapted for use in variously configured medication delivery devices, including differently constructed pen-shaped medication injection devices, differently shaped injection devices, and infusion pump devices. The medication may be any of a type that may be delivered by such a medication delivery device. Device is intended to be illustrative and not limiting as the sensing system described further below may be used in other differently configured devices.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. A medication delivery device including: a device body; a dose setting member attached to the device body and rotatable relative to the device body about an axis of rotation during dose delivery; a sensed element attached to and rotationally fixed with the dose setting member, the sensed element including axially extending surface features radially-spaced from one another about the axis of rotation of the dose setting member; an actuator attached to the device body, wherein the sensed element is rotatable relative to the actuator during dose delivery in relation to the amount of dose delivered; a rotational sensor attached to the actuator, the rotational sensor including a movable element positionable to slidably contact the axially extending surface features during rotation of the sensed element relative to the actuator during dose delivery, the rotational sensor configured to generate a signal in response to a triggering of the movable element over the axially extending surface features during the rotation of the dose setting member; and a controller operatively coupled to the rotational sensor, wherein, in response to receiving the generated signal from the rotational sensor, the controller is configured to determine a number of the axially extending surface features passing the movable element of the rotational sensor during dose delivery.

2. The medication delivery device of aspect 1, wherein the axially extending surface features include alternating projections and recesses, the movable element riding against the projections and recesses during rotation of the sensed element relative to the actuator during dose delivery.

3. The medication delivery device of aspect 2, wherein the projections extend proximally from the dose setting member.

4. The medication delivery device of any one of aspects 1-3, wherein the dose setting member is a flange or a dose dial member.

5. The medication delivery device of any one of aspects 1-4, wherein the rotational sensor includes a switch, wherein the movable element alternately engaging or disengaging the axially extending surface features is operable to trigger the switch and generate the signal.

6. The medication delivery device of any one of aspects 1-5, wherein the actuator has a first position in which the movable element of the rotational sensor is disengaged from the axially extending surface features.

7. The medication delivery device of aspect 6, wherein the actuator has a second position in which the movable element of the rotational sensor is contactable with the axially extending surface features.

8. The medication delivery device of aspect 7, wherein, when the actuator is in the second position, the controller is configured, upon receiving a signal indicative of contact with an initial first one of the axially extending surface features, to activate the controller to a full power state, and the controller is configured, upon receiving a signal indicative of contact with a subsequent one of the axially extending surface features after the initial first one, to determine a number of the axially extending surface features passing the movable element of the rotational sensor during dose delivery.

9. The medication delivery device of any one of aspects 1-8, wherein the movable element includes at least one contact by which upon engagement with the axially extending surface features is operable to generate the signal.

10. The medication delivery device of aspect 9, wherein the at least one contact include a pair of contacts, wherein upon engagement of one of the pair of contacts with the axially extending surface is configured to move into contact with the other of the pair of contacts to generate the signal.

11. The medication delivery device of any one of aspects 1-8, wherein movement of the movable element relative to the axially extending surface features is configured to generate rotation vibrations, wherein the rotational sensor is configured to generate the signal in response to detection of the rotation vibrations.

12. The medication delivery device of aspect 11, wherein the rotational sensor includes a rotation accelerometer operable to detect the rotation vibrations.

13. The medication delivery device of aspect 12, wherein the rotational sensor further includes a ground accelerometer operable to detect ground vibrations, the controller is configured to compare the rotation and ground vibrations and configured to determine vibrations indicative of rotation of the sensed element relative to the actuator during dose delivery from the comparison.

14. The medication delivery device of any one of aspects 1-8, wherein movement of the movable element relative to the axially extending surface features is configured to generate rotation sounds, wherein the rotational sensor is configured to generate the signals in response to detection of the rotation sounds.

15. The medication delivery device of any one of aspects 1-14, further including a module removably attached to the actuator, the module including the movable element for engagement with the sensed element of the dose setting member of the device body that is outside the module.

16. The medication delivery device of any one of aspects 1-8, wherein the rotational sensor includes a piezoelectric sensor.

17. A medication delivery device including: a device body; a dose setting member attached to the device body and rotatable relative to the device body about an axis of rotation during dose delivery, wherein the dose setting member includes a sensed element, the sensed element including surface features radially-spaced from one another about the axis of rotation of the dose setting member; a dose button attached to the device body, wherein the sensed element is rotatable relative to the dose button during dose delivery in relation to the amount of dose delivered, wherein the dose button houses a rotational sensor, the rotational sensor including a movable element positionable to slidably contact the surface features during rotation of the sensed element relative to the dose button during dose delivery, the rotational sensor configured to generate a signal in response to the movement of the movable element over the surface features during the rotation of the dose setting member, wherein the dose button has a first position in which the movable element of the rotational sensor is disengaged from the surface features, and a second position in which the movable element of the rotational sensor is contactable with the surface features; and a controller operatively coupled to the rotational sensor and housed by the dose button, wherein, in response to receiving the generated signal from the rotational sensor, the controller is configured to determine a number of the surface features passing the movable element of the rotational sensor during dose delivery, wherein, when the dose button is in the second position, the controller is configured, upon receiving a signal indicative of contact with an initial first one of the surface features, to activate the controller to a full power state, and the controller is configured, upon receiving a signal indicative of contact with a subsequent one of the surface features after the initial first one, to determine a number of the axially extending surface features passing the movable element of the rotational sensor during dose delivery.

18. The medication delivery device of aspect 17, wherein the rotational sensor includes a switch.

19. The medication delivery device of aspect 17, wherein the rotational sensor includes at least one contact.

20. The medication delivery device of aspect 17, wherein the rotational sensor includes a piezoelectric sensor.

21. The medication delivery device of aspect 17, wherein the surface features axially extend from the dose setting member.

22. The medication delivery device of any one of the preceding aspects, further comprising a bias member axially disposed between the dose button and the dose setting member, wherein the rotational sensor and the controller are disposed within a cavity of the dose button, and the surface features are disposed within the cavity radially outside the bias member.

23. The medication delivery device of any one of the preceding aspects, wherein the device body includes a reservoir having a medication.

We claim:

1. An electronic system for a drug delivery device, the electronic system comprising:
   a dose setting and drive mechanism which is configured to perform a dose setting operation for setting a dose to be delivered by the drug delivery device and a dose delivery operation for delivering the set dose,
   the dose setting and drive mechanism comprising a first member and a second member, wherein the dose setting and drive mechanism is configured such that, in the dose delivery operation, the first member rotates relative to the second member,
   an electronic control unit configured to control an operation of the electronic system, the electronic system having a first state and a second state, wherein the electronic system has an increased electrical power consumption in the second state as compared to the first state,
   an electrical use detection unit, the electrical use detection unit being operatively connected to the electronic control unit, the electrical use detection unit being configured to generate a use signal which indicates that the user has commenced the dose delivery operation, wherein:
   the first member is provided with circumferentially disposed teeth;
   the electronic system comprises a switch which is operatively coupled to the second member and which is arranged to cooperate with the teeth during rotation of the first member relative to the second member during the dose delivery operation, wherein the switch comprises a pair of contacts that are configured to generate the use signal by moving into contact with one another when the switch is engaged by one of the teeth during the rotation of the first member relative to the second member; and
   the electronic system is configured such that it is switched from the first state into the second state by the electronic control unit in response to the use signal.

2. The electronic system of claim 1, wherein the switch is pivotally mounted, and wherein at least part of of the switch is configured to move pivotally when the switch is engaged by one of the teeth.

3. The electronic system of claim 1, wherein the first member is configured to move during the dose delivery operation relative to a housing of the electronic system or the drug delivery device.

4. The electronic system of claim 1, wherein the first member is a dose dial member and the second member is an actuator.

5. A drug delivery device comprising the electronic system of claim 1 and a reservoir with a drug in the drug delivery device.

* * * * *